(12) United States Patent
Goodrich et al.

(10) Patent No.: US 10,590,218 B2
(45) Date of Patent: Mar. 17, 2020

(54) POLYMER COMPOSITIONS WITH ENHANCED RADIOPACITY

(71) Applicant: ENDOSHAPE, INC., Boulder, CO (US)

(72) Inventors: Stephen D. Goodrich, Longmont, CO (US); Jeffrey P. Castleberry, Longmont, CO (US)

(73) Assignee: ENDOSHAPE, INC., Boulder, CO (US)

(*) Notice: Subject to any disclaimer, the term of this patent is extended or adjusted under 35 U.S.C. 154(b) by 211 days.

(21) Appl. No.: 14/776,875

(22) PCT Filed: Mar. 14, 2014

(86) PCT No.: PCT/US2014/028786
§ 371 (c)(1),
(2) Date: Sep. 15, 2015

(87) PCT Pub. No.: WO2014/200594
PCT Pub. Date: Dec. 18, 2014

(65) Prior Publication Data
US 2016/0024239 A1 Jan. 28, 2016

Related U.S. Application Data

(60) Provisional application No. 61/787,345, filed on Mar. 15, 2013.

(51) Int. Cl.
*C08F 220/22* (2006.01)
*A61K 49/04* (2006.01)
(Continued)

(52) U.S. Cl.
CPC ........ *C08F 220/22* (2013.01); *A61K 49/0442* (2013.01); *A61L 29/041* (2013.01);
(Continued)

(58) Field of Classification Search
CPC ............... C08F 220/22; C08F 220/30; C08F 222/1006; A61K 49/0442; A61L 29/18; A61L 31/18
See application file for complete search history.

(56) References Cited

U.S. PATENT DOCUMENTS 3,361,700 A    1/1968  Archer et al.
4,644,025 A *  2/1987  Sakagami ............. C08F 218/12
                                                359/642
(Continued)

FOREIGN PATENT DOCUMENTS

EP    0710475       5/1996
EP    2968620 B1    2/2019
(Continued)

OTHER PUBLICATIONS

First Office Action dated Apr. 28, 2017, corresponding the Chinese Patent Application No. 201480027781.1 (including English translation).
(Continued)

*Primary Examiner* — Ling Siu Choi
*Assistant Examiner* — David L Miller
(74) *Attorney, Agent, or Firm* — Leydig, Voit & Mayer, Ltd.

(57) ABSTRACT

Radiopaque polymer compositions and methods for making the compositions are provided. These radiopaque polymer compositions include polymer compositions comprising a crosslinked polymer network, the network comprising a first repeating unit derived from a monofunctional monomer and a second repeating unit derived from a crosslinker monomer or oligomer having more than two polymerizable groups. Devices formed from radiopaque polymer compositions are also provided.

16 Claims, 5 Drawing Sheets

(51) Int. Cl.

| | | |
|---|---|---|
| C08F 222/10 | (2006.01) | |
| C08F 220/30 | (2006.01) | |
| A61L 29/04 | (2006.01) | |
| A61L 29/18 | (2006.01) | |
| A61L 31/04 | (2006.01) | |
| A61L 31/18 | (2006.01) | |

(52) U.S. Cl.
CPC ............. *A61L 29/18* (2013.01); *A61L 31/048* (2013.01); *A61L 31/18* (2013.01); *C08F 220/30* (2013.01); *C08F 222/1006* (2013.01); *A61L 2400/16* (2013.01); *C08F 2220/303* (2013.01)

(56) References Cited

U.S. PATENT DOCUMENTS

| | | |
|---|---|---|
| 5,163,952 A | 11/1992 | Froix |
| 5,258,020 A | 2/1993 | Froix |
| 5,271,923 A | 12/1993 | Kochi et al. |
| 5,525,327 A | 6/1996 | Baker et al. |
| 5,599,291 A | 2/1997 | Balbierz |
| 5,674,241 A | 10/1997 | Bley |
| 5,674,242 A | 10/1997 | Phan |
| 5,679,710 A | 10/1997 | Davy et al. |
| 5,780,668 A * | 7/1998 | Rheinberger ........ A61K 6/083 433/215 |
| 5,964,744 A | 10/1999 | Balbierz |
| 6,040,408 A | 3/2000 | Koole |
| 6,068,969 A * | 5/2000 | Mikoshiba ........ G03C 7/3008 430/384 |
| 6,160,084 A | 12/2000 | Langer et al. |
| 6,248,129 B1 | 6/2001 | Froix |
| 6,388,043 B1 | 5/2002 | Langer et al. |
| 6,475,477 B1 | 11/2002 | Kohn et al. |
| 6,509,406 B1 | 1/2003 | Brenner et al. |
| 6,550,480 B2 | 4/2003 | Feldman |
| 6,720,402 B2 | 4/2004 | Langer et al. |
| 6,887,266 B2 | 5/2005 | Williams |
| 7,115,691 B2 | 10/2006 | Alvarado |
| 7,208,550 B2 | 4/2007 | Mather |
| 7,217,744 B2 | 5/2007 | Lendlein et al. |
| 7,250,154 B2 | 7/2007 | Kohn et al. |
| 7,473,417 B2 | 1/2009 | Zeltinger et al. |
| 7,553,325 B2 | 6/2009 | Stinson |
| 9,062,141 B2 | 6/2015 | Goodrich et al. |
| 2004/0030062 A1 | 2/2004 | Mather |
| 2005/0033163 A1 | 2/2005 | Duchon et al. |
| 2005/0106119 A1 | 5/2005 | Brandom et al. |
| 2006/0024266 A1 | 2/2006 | Brandom et al. |
| 2006/0034769 A1 | 2/2006 | Kohn et al. |
| 2006/0036045 A1 | 2/2006 | Wilson |
| 2006/0036316 A1 | 2/2006 | Zeltinger et al. |
| 2006/0041089 A1 | 2/2006 | Mather |
| 2006/0095134 A1 | 5/2006 | Trieu et al. |
| 2006/0142794 A1 | 6/2006 | Lendlein et al. |
| 2006/0182779 A1 | 8/2006 | Brandom et al. |
| 2006/0213522 A1 | 9/2006 | Menchaca et al. |
| 2008/0009939 A1 | 1/2008 | Guerigian et al. |
| 2008/0228186 A1 | 9/2008 | Gall et al. |
| 2008/0281405 A1 | 11/2008 | Williams et al. |
| 2009/0023827 A1 | 1/2009 | Lendlein et al. |
| 2009/0248141 A1 | 10/2009 | Shandas et al. |
| 2011/0144227 A1 | 6/2011 | Bowman et al. |
| 2013/0109777 A1 | 5/2013 | Eckert et al. |
| 2013/0225778 A1 | 8/2013 | Goodrich et al. |
| 2015/0374884 A1 | 12/2015 | Goodrich |

FOREIGN PATENT DOCUMENTS

| | | |
|---|---|---|
| GB | 1526888 | 10/1978 |
| GB | 2085012 | 4/1982 |
| JP | 62-001708 A | 1/1987 |
| JP | 08-325203 A | 12/1996 |
| JP | 2002-182002 A | 6/2002 |
| JP | 2004-342537 A | 12/2004 |
| JP | 2006-77200 A | 3/2006 |
| JP | 2007-279585 A | 10/2007 |
| JP | 2010-186979 A | 8/2010 |
| JP | 2013-530229 T | 7/2013 |
| JP | 2013-538262 T | 10/2013 |
| WO | WO2005/109041 | 11/2005 |
| WO | WO2006/020616 | 2/2006 |
| WO | WO2007/084444 | 7/2007 |
| WO | WO2007/114823 | 10/2007 |
| WO | WO2007/115208 | 10/2007 |
| WO | WO2007/143698 | 12/2007 |
| WO | WO2008/033198 | 3/2008 |
| WO | WO2008/051279 | 5/2008 |
| WO | WO2008/054205 | 5/2008 |
| WO | WO2008/137235 | 11/2008 |
| WO | WO2008/138974 | 11/2008 |
| WO | WO 2012/003136 | 1/2012 |
| WO | WO2012/019145 | 2/2012 |
| WO | WO 2012019145 A1 * | 2/2012 ......... A61K 49/0442 |

OTHER PUBLICATIONS

Aldenhoff et al. (2002) "Stability of radiopaque iodine-containing biomaterials," Biomaterials. 23(3):881-886.

Benzina et al. (Nov. 1994) "Studies on a new radiopaque polymeric biomaterial," Biomaterials. 15(14):1122-8.

Benzina et al. (Nov. 1996) "A versatile three-iodine molecular building block leading to new radiopaque polymeric biomaterials," J. Biomed. Mater. Res. 32(3):459-66.

Chappard et al. (Nov. 2008) "Chemical structure of methylmethacrylate-2-[2',3',5'-triiodobenzoyl]oxoethyl methacrylate copolymer, radio-opacity, in vitro and in vivo biocompatibility," Acta Biomaterials. 4(6):1762-1769.

Constant et al. (Sep. 2008) "Preparation, characterization, and evaluation of radiopaque hydrogel filaments for endovascular embolization," J. Biomed. Mater. Res. Part B: Appl. Biomater. 89B(2):306-313.

Cui et al. (Apr. 17, 2009) "Shape-Memory Properties of Radiopaque Micro-Composites from Amorphous Polyether Urethanes Designed for Medical Application," MRS Spring Meeting Materials Research Society.

Davy et al. (1997) "X-Ray Opaque Methacrylate Polymers for Biomedical Applications," Polymer International. 43:143-154.

Davy et al. (1996) "Novel iodinated methacrylates as X-ray opaque denture base polymers," J. Materials Science Letters. 35:656-657.

De Nardo et al. (Dec. 2008) "Shape memory polymer foams for cerebral aneurysm reparation: Effects of plasma sterilization on physical properties and cytocompatibility," Acta Biomaterialia. 5:1508-1518.

Galperin et al. (2006) "Synthesis and characterization of new radiopaque microspheres by the dispersion polymerization of an iodinated acrylate monomer for X-ray imaging applications," J. Polymer Sci. Part A: Polymer Chem. 44(12):3959-3868.

Galperin et al. (2007) "Radiopaque iodinated polymeric nanoparticles for X-ray imaging applications," Biomaterials. 28(30):4461-4468.

Hampikian et al. (2006) "Mechanical and radiographic properties of a shape memory polymer composite for intracranial aneurysm coils," Mater. Sci. Engr. C. 26:1373-1379.

Heaton (Jul. 2004) "A Shape Memory Polymer for Intracranial Aneurysm Coils: An Investigation of Mechanical and Radiographic Properties of a Tantalum-Filled Shape Memory Polymer Composite," Thesis, Georgia Institute of Technology.

Jeon et al. (Jul. 2000) "Shape memory and nanostructure in poly(norbornyi-POSS) copolymers," Polymers International. 29:453-457.

Jeong et al. (2000) "Shape memory polyurethane containing amorphous reversible phase," J. Mat. Sci. 35:1579-1583.

Lendlein (2002) "Biodegradable, elastic shape-memory polymers for potential biomedical applications," Science. 296:1673-1676.

Lendlein et al. (2001) "AB-polymer networks based on oligo(epsilon-caprolactone) segments showing shape-memory properties," Proc. Nat. Acad. Sci. 98:3.842-847.

(56) References Cited

OTHER PUBLICATIONS

Lendlein et al. (2002) "Shape Memory Polymer," Advanced Chemie, International Edition. 41:2034-2057.
Li et al. (1999) "Shape memory effect of ethylene-vinyl acetate copolymers," J. App. Poly. Sci. 71:1063-1070.
Li et al. (2002) "New Soybean Oil-Styrene-Divinylbenzene Thermosetting Copolymers. V. Shape memory effect," J. App. Pol. Sci. 84:1533-1543.
Lin et al. (1998) "Study on Shape-Memory Behavior of Polyether-Based Polyurethanes. I. Influence of the Hard-Segment Content," J. App. Pol. Sci. 69:1563-1574.
Lin et al. (Aug. 22, 1998) "Study on Shape-Memory Behavior of Polyether-Based Polyurethanes. II. Influence of soft-segment molecular weight," Journal of Applied Polymer Science. 69(8):1575-1586.
Liu et al. (2002) "Chemically cross-linked polycyclooctene: Synthesis, characterization, and shape memory behavior," Macromolecules. 35:27.9868-9874.
Liu et al. (2003) "Thermomechanical Recovery Couplings of Shape Memory Polymers in Flexure," Smart Materials & Structures. 12:947-954.
Maitland (May 2007) "Prototype laser-activated shape memory polymer foam device for embolic treatment of aneurysms," J. Biomedical Optics (Letters). 12(3).030504-1-030504-3.
Moszner et al. (1995) "Synthesis and polymerization of hydrophobic iodine-containing methacrylates," Die Angewandte Makromolekulare Chemie. 224:115-123.
Sillion (2002) "Shape memory polymers," Act. Chimique. 3:182-188.
Small et al. (Mar. 2010) "Biomedical applications of thermally activated shape memory polymers," Journal of Materials Chemistry. 20:3356-3366.
Takahashi et al. (1996) "Structure and properties of shape memory polyurethane block copolymers," J. App. Pol. Sci. 60:1061-1069.
Van Hooy-Corstjens et al. (2004) "Mechanical behavior of a new acrylic radiopaque iodine-containing bone cement," Biomater. 25:2657-2667.
Wilson et al. (2005) "Shape Memory Polymer Therapeutic Devices for Stroke," Proc. of SPIE. 6007-60070R:60070R-1-60070R-8.
Yakacki et al. (2008) "Cytotoxicity and Thermomechanical behavior of biomedical shape memory polymer networks post sterilization," Biomedical Materials. 3:015010.9.
Zaharia (2008) "Chemical structure of methylmethacrylate-2[2',3',5'-triiodobenzoyl] oxoethyl methacrylate copolymer, radioopacity, in vitro and in vivo biocompatibility," Acta Biomaterialia. 4:1762-1769.
Zhu et al. (2003) "Shape-memory effects of radiation crosslinked poly(epsilon-caprolactone)," J. App. Poly. Sci. 90:1589-1595.
International Search Report and Written Opinion corresponding to International Patent Application No. PCT/US14/28786, dated Nov. 20, 2014.
Supplementary European Search Report corresponding to European Patent Application No. EP14811002, dated Sep. 7, 2016.
First Examination Report dated Mar. 9, 2018 for Australian Patent Application No. 2014278745.
Notice of Reasons for Rejected dated Feb. 6, 2018 for Japanese Patent Application No. P2016-502897 (including English translation).
Second Office Action dated Dec. 14, 2017 for Chinese Patent Application No. 2014800277811 (including partial English translation).
Japanese Notice of Reasons for Rejected dated Oct. 16, 2018 for Japanese Patent Application No. P2016-502897 (including English translation).
Third Office Action dated Jul. 3, 2018 for Chinese Patent Application No. 2014800277811 (including English translation).
Australian Second Examination Report issued in Australian Application Serial No. 2014278745 dated Jan. 7, 2019.
Chinese Fourth Office Action issued in Chinese Application Serial No. 2014800277811 dated Nov. 27, 2018.
Chinese Decision of Rejection issued in Chinese Application Serial No. 2014800277811 dated Mar. 5, 2019.

* cited by examiner

POLYMER COMPOSITIONS WITH ENHANCED RADIOPACITY

CROSS-REFERENCE TO RELATED APPLICATIONS

This application is a U.S. National Stage Application under 35 U.S.C. § 371 of International Application No. PCT/US2014/028786, filed Mar. 14, 2014, which claims the benefit of U.S. Provisional Application No. 61/787,345, filed Mar. 15, 2013, each of which is hereby incorporated by reference in its entirety.

STATEMENT REGARDING FEDERALLY SPONSORED RESEARCH OR DEVELOPMENT

Not applicable.

BACKGROUND OF THE INVENTION

Shape memory materials are defined by their capacity to recover a predetermined shape after significant mechanical deformation (K. Otsuka and C. M. Wayman, "Shape Memory Materials" New York: Cambridge University Press, 1998). The shape memory effect can be initiated by a number of stimuli including by a change in temperature and has been observed in metals, ceramics, and polymers. From a macroscopic point of view, the shape memory effect in polymers differs from ceramics and metals due to the lower stresses and larger recoverable strains achieved in polymers.

The basic thermomechanical response of shape memory polymer (SMP) materials is defined by four critical temperatures. The glass transition temperature, $T_g$, is typically represented by a transition in modulus-temperature space and can be used as a reference point to normalize temperature for some SMP systems. SMPs offer the ability to vary $T_g$ over a temperature range of several hundred degrees by control of chemistry or structure. The predeformation temperature, $T_d$, is the temperature at which the polymer is deformed into its temporary shape. Depending on the required stress and strain level, the initial deformation $T_d$ can occur above or below $T_g$ (Y. Liu, K. Gall, M. L. Dunn, and P. McCluskey, "Thermomechanical Recovery Couplings of Shape Memory Polymers in Flexure." Smart Materials & Structures, vol. 12, pp. 947-954, 2003). The storage temperature, $T_s$, represents the temperature in which no shape recovery occurs and is equal to or is below $T_d$. The storage temperature $T_s$ is less than the glass transition temperature $T_g$. At the recovery temperature, $T_r$, the shape memory effect is activated, which causes the material to substantially recover its original shape. $T_r$ is above $T_s$ and is typically in the vicinity of $T_g$. Recovery can be accomplished isothermally by heating the material to a fixed $T_r$ and then holding, or by continued heating up to and past $T_r$. From a macroscopic viewpoint, a polymer will demonstrate a useful shape memory effect if it possesses a distinct and significant glass transition (B. Sillion, "Shape memory polymers," Act. Chimique., vol. 3, pp. 182-188, 2002), a modulus-temperature plateau in the rubbery state (C. D. Liu, S. B. Chun, P. T. Mather, L. Zheng, E. H. Haley, and E. B. Coughlin, "Chemically cross-linked polycyclooctene: Synthesis, characterization, and shape memory behavior." Macromolecules. vol. 35, no. 27, pp. 9868-9874, 2002), and a large difference between the maximum achievable strain, $\varepsilon_{max}$, during deformation and permanent plastic strain after recovery, $\varepsilon_p$ (F. Li, R. C. Larock, "New Soybean Oil-Styrene-Divinylbenzene Thermosetting Copolymers. V. Shape memory effect." J. App. Pol. Sci., vol. 84, pp. 1533-1543, 2002). The difference $\varepsilon_{max}-\varepsilon_p$ is defined as the recoverable strain, $\varepsilon_{recover}$, while the recovery ratio is defined as $\varepsilon_{recover}/\varepsilon_{max}$.

The microscopic mechanism responsible for shape memory in polymers depends on both chemistry and structure (T. Takahashi, N. Hayashi, and S. Hayashi, "Structure and properties of shape memory polyurethane block copolymers." J. App. Pol. Sci., vol. 60, pp. 1061-1069, 1996; J. R. Lin and L. W. Chen, "Study on Shape-Memory Behavior of Polyether-Based Polyurethanes. II. Influence of the Hard-Segment Content." J. App. Pol. Sci., vol. 69, pp. 1563-1574, 1998; J. R. Lin and L. W. Chen, "Study on Shape-Memory Behavior of Polyether-Based Polyurethanes. I. Influence of soft-segment molecular weight." J. App. Pol. Sci., vol 69, pp. 1575-1586, 1998; F. Li, W. Zhu, X. Zhang, C. Zhao, and M. Xu, "Shape memory effect of ethylene-vinyl acetate copolymers." J. App. Poly. Sci., vol., 71, pp. 1063-1070, 1999; H. G. Jeon, P. T. Mather, and T. S. Haddad, "Shape memory and nanostructure in poly(norbornyl-POSS) copolymers." Polym. Int., vol. 49, pp. 453-457, 2000; H. M. Jeong, S. Y. Lee, and B. K. Kim, "Shape memory polyurethane containing amorphous reversible phase." J. Mat. Sci., vol. 35, pp. 1579-1583, 2000; A. Lendlein, A. M. Schmidt, and R. Langer, "AB-polymer networks based on oligo (epsilon-caprolactone) segments showing shape-memory properties." Proc. Nat. Acad. Sci., vol. 98, no. 3, pp. 842-847, 2001; G. Zhu, G. Liang, Q. Xu, and Q. Yu, "Shape-memory effects of radiation crosslinked poly(epsilon-caprolactone)." J. App. Poly. Sci., vol. 90, pp. 1589-1595, 2003). One driving force for shape recovery in polymers is the low conformational entropy state created and subsequently frozen during the thermomechanical cycle (C. D. Liu, S. B. Chun, P. T. Mather, L. Zheng, E. H. Haley, and E. B. Coughlin, "Chemically cross-linked polycyclooctene: Synthesis, characterization, and shape memory behavior." Macromolecules. Vol. 35, no. 27, pp. 9868-9874, 2002). If the polymer is deformed into its temporary shape at a temperature below $T_g$, or at a temperature where some of the hard polymer regions are below $T_g$, then internal energy restoring forces will also contribute to shape recovery. In either case, to achieve shape memory properties, the polymer must have some degree of chemical crosslinking to form a "memorable" network or must contain a finite fraction of hard regions serving as physical crosslinks.

SMPs are processed in a manner that is termed programming, whereby the polymer is deformed and set into a temporary shape. (A. Lendlein, S. Kelch, "Shape Memory Polymer," Advanced Chemie, International Edition, 41, pp. 1973-2208, 2002.) When exposed to an appropriate stimulus, the SMP substantially reverts back to its permanent shape from the temporary shape. The stimulus may be, for example, temperature, magnetic field, water, or light, depending on the initial monomer systems.

For SMPs used in medical devices, wherein temperature is the chosen stimulus, an external heat source may be used to provide discretionary control of the shape recovery by the physician, or the body's core temperature may be utilized to stimulate the shape recovery upon entry or placement within the body from the environmental temperature, which may be room temperature. (Small W, et al. "Biomedical applications of thermally activated shape memory polymers" Journal of Materials Chemistry, Vol 20, pp 3356-3366, 2010.)

For implantable medical devices, the life expectancy of the device can be defined by the duration that it must maintain its mechanical properties and functionality in the body. For biodegradable devices, this life expectancy is intentionally short, providing a mechanism for the material and device to degrade over time and be absorbed by the body's metabolic processes. For non-biodegradable devices, referred to as biodurable devices, or devices exhibiting biodurability, they are not intended to degrade and they must maintain their material properties and functionality for longer periods, possibly for the life the patient.

For medical devices used within the body, either permanent implants or instrumentation used for diagnostic or therapeutic purposes, the ability to visualize the device using typical clinical imaging modalities, e.g. X-ray, Fluoroscopy, CT Scan, and MRI is typically a requirement for clinical use. Devices intended to be imaged by X-ray and Fluoroscopy, typically contain either metals or metal byproducts to induce radiopacity. Radiopacity refers to the relative inability of electromagnetism, particularly X-rays, to pass through dense materials, which are described as 'radiopaque' appearing opaque/white in a radiographic image. A more radiopaque material appears brighter, whiter, on the image. (Novelline, Robert. Squire's Fundamentals of Radiology. Harvard University Press. 5th edition. 1997.) Given the complexity of the content within an X-ray or Fluoroscopic image, clinicians are sensitive to the quality of the image regarding the brightness or signal strength of the material in the image. The two main factors that contribute to radiopacity brightness, or signal strength of a material are density and atomic number. Polymer based medical devices requiring radiopacity typically utilize a polymer blend that incorporates a small amount, by weight percent, of a heavy atom, radiopaque filler such as Titanium Dioxide ($TiO_2$), or Barium Sulfate ($BaSO_4$). The device's ability to be visualized on fluoroscopy is dependent upon the amount, or density, of the filler mixed into the material, which is typically limited to a small quantity as the filler can detrimentally affect the base polymer's material properties. Meanwhile, medical device imaging companies have developed standardized liquid contrast media to be intermittently used by physicians to highlight vascular structures, etc. during X-ray or Fluoroscopy when filled with this contrast media. This media commonly contains a heavy atom fluid, such as iodine, to induce radiopacity.

Iodine-incorporating monomers were reported by Mosner et al., who reported 3 different triiodinated aromatic monomers, which differed in the degree to which they could be homopolymerized or required copolymerization in order to be incorporated. (Moszner et al. "Synthesis and polymerization of hydrophobic iodine-containing methacrylates" Die Angewandte Makromolekulare Chemie 224 (1995) 115-123) Iodinating monomers was also pursued by Koole et al. in the Netherlands, as published from 1994-1996 with a range of monoiodinated to triiodinated aromatic monomers (Koole et al. "Studies on a new radiopaque polymeric biomaterial," Biomaterials 1994 November; 15(14):1122-8. Koole et al. "A versatile three-iodine molecular building block leading to new radiopaque polymeric biomaterials," J Biomed Mater Res, 1996 November; 32(3):459-66). This included biocompatibility results of a 2-year implantation study in rats of monoiodinated aromatic methacrylate copolymer systems. (Koole et al. "Stability of radiopaque iodine-containing biomaterials," Biomaterials 2002 February; 23(3):881-6) They are also discussed by Koole in U.S. Pat. No. 6,040,408, filed initially as a European patent application in August, 1994, which limits its claims to aromatic monomers containing no more than two covalently bonded iodine groups. (U.S. Pat. No. 6,040,408, "Radiopaque Polymers and Methods for Preparation Thereof," Koole, 21 Mar. 2000). Also, US Patent Application 20060024266 by Brandom et al. claimed polyiodinated aromatic monomers in shape memory polymers, emphasizing the use of crystallizable polymer side-groups (US Patent Application 20060024266, "Side-chain crystallizable polymers for medical applications, Brandom et al., 5 Jul. 2005).

WO 2012/019145 and U.S. Ser. No. 61/762,416 describe shape memory materials having crosslinked radiopaque iodinated aromatic monomers. Both of these applications are hereby incorporated by reference in their entirety.

Materials, including shape memory polymers, having useful properties including enhanced radiopacity are desired. As a specific example, shape memory materials with enhanced radiopacity that is useful for imaging biomaterial implants of small size and thickness while retaining critical performance properties, including rapid shape retention upon emergence from a deployment catheter and mechanical durability to prevent fracture and release of fragments, is desired.

BRIEF SUMMARY OF THE INVENTION

Provided generally are radiopaque polymers, compositions or materials that have useful radiopacity properties. Useful radiopacity properties include enhanced radiopacity. As used herein, "enhanced radiopacity" is not intended to reflect a particular numerical value or absolute measure of radiopacity, but rather refers to a composition having a radiopacity quality that is useful for the desired purpose. In one aspect, enhanced radiopacity is useful for imaging the polymers described herein and devices incorporating the polymers described herein. In one aspect, enhanced radiopacity is useful for allowing the polymers described herein to be formulated into materials and devices having desirable properties, including smaller size and/or narrower thickness, than materials and devices that do not use the polymers described herein. As used herein and unless contrary to the specific usage, the terms "materials," "polymers," "compositions," "composites" and other similar terms are used to refer to a polymer material made from monomer moieties and other groups as described herein.

In one aspect, enhanced radiopacity is a result of the amount of radiopaque monomer used to form the polymer compositions of the invention. In an embodiment, the loading of radiopaque moeities in the materials of the invention is higher than in other materials, without inducing brittleness in the present materials. In an embodiment, higher loading of radiopaque monomer in the polymer precursor mixture used to form the polymer compositions of the invention is possible through the use of a clustered crosslinker, as described further herein. In an aspect, the clustered crosslinker is more efficient in crosslinking other parts of the composition than other crosslinkers. In some materials described herein, the enhanced radiopacity is reflected in a higher wt % of radiopaque element in the polymer (such as iodine, bromine or bismuth) than other materials.

In one aspect, the radiopaque polymers disclosed are shape memory polymers (SMPs). In one aspect, the compositions and compounds disclosed are useful for medical devices. In one aspect, the compositions and compounds disclosed may be shape memory polymers as defined herein and known in the art, but are not used in a manner in which the shape memory property is used. In one aspect, the compounds and compositions may or may not be externally triggered. In one aspect, the compositions and compounds disclosed are "space-triggered", as the phrase is conventionally used. In a space triggered material the materials return to their original shape upon removal of a spatial constraint, as is the case when a coil-shaped specimen emerges from its temporary elongated configuration within a deployment catheter and regains its coil shape, for example. In one aspect, the composition and compounds disclosed herein are "thermally-triggered," as the phrase is conventionally used. In a thermally triggered material the materials return to their original shape upon a thermal stimulus.

It should be made clear that certain compositions and compounds described herein may technically have shape memory properties, but those properties may or may not be used in the devices and methods of the invention. As used herein, the compounds and compositions described and disclosed here are intended to include shape memory aspects and non-shape memory aspects as applicable. If a particular embodiment is described using a shape memory polymer, it is recognized that other compounds and compositions that are not specifically defined as having shape memory properties may be interchangeable and used in that embodiment.

In an aspect, provided is a polymer composition obtained by the polymerization of a first reactant comprising a radiopaque functionality and a second reactant comprising three or more polymerizable groups. In an embodiment, the polymer composition is crosslinked. The polymer composition comprises a plurality of repeating units derived from the first reactant and a plurality of repeating units derived from the second reactant. In an embodiment, the first reagent comprises one or more monomers including iodine, or bromine or bismuth and also including a polymerizable group. The second reagent comprises a crosslinking reagent. Crosslinking reagents useful for the present invention include monomers or oligomers which are branched and which comprise at least three terminal polymerizable groups, but which do not comprise iodine, bromine or bismuth. In an embodiment, the terminal polymerizable groups are located at the ends of branches. The crosslinking monomer or oligomer may comprise at least three (meth) acrylate, (meth)acrylamide or styryl groups. In other embodiments, the monomer or oligomer may comprise from 3 to 20, from 6 to 20 or from 8 to 20 polymerizable groups. The crosslinking monomer or oligomer may further comprise one or more terminal functional groups other than polymerizable groups. For example, the crosslinking monomer or oligomer may further comprise one or more terminal acyl chloride, carboxyl, ester or amide groups In an embodiment, the weight percentage of the repeating units derived from the first reagent is from 65-95 wt %, from 79-90 wt % or from 75-85 wt % and the weight percentage of the repeating units derived from the second reagent is from 5 to 35 wt %, from 10 to 30 wt % or from 15 to 25 wt %. Also provided is a crosslinked polymer composition comprising the polymerized composition of claim 1.

Reagents including iodine, bromine or bismuth useful for the present invention include monomers represented by the structure of Formula 1, Formula 1-A, Formula 1-B or Formula 1-C, where the terms in the formulas are as described below.

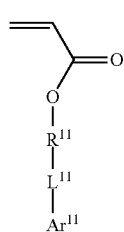

Formula 1

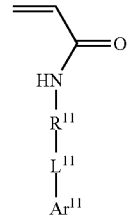

Formula 1-A

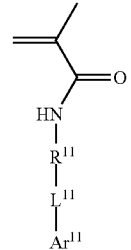

Formula 1-B

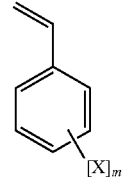

Formula 1-C

In Formula 1, Formula 1-A, Formula 1-B and Formula 1-C:
X is Br or I;
m in Formula 1-C is 1-5;
each $R^{11}$ is independently a substituted or unsubstituted $C_2$-$C_{36}$ alkylene group; $C_3$-$C_{36}$ cycloalkylene group; $C_2$-$C_{36}$ alkenylene group; $C_3$-$C_{36}$ cycloalkenylene group; $C_2$-$C_{36}$ alkynylene group; $C_5$-$C_{36}$ arylene group; or $C_5$-$C_{36}$ heteroarylene group;
each $L^{11}$ is independently a single bond; —$(CH_2)_q$—; —$(HCCH)_q$—; —O—; —S—; —SO—; —$SO_2$—; —$SO_3$—; —$OSO_2$—; —$NR^{12}$—; —CO—; —COO—; —OCO—; —OCOO—; —$CONR^{13}$—; —$NR^{14}CO$—; —$OCONR^{15}$—, —$NR^{16}COO$—, or —$NR^{17}CONR^{18}$—;
each $Ar^{11}$ is independently an iodine-, bromine or bismuth-containing $C_5$-$C_{36}$ aryl group containing one or more rings, or an iodine-, bromine or bismuth-containing $C_5$-$C_{36}$ heteroaryl group containing one or more rings;
each of $R^{12}$-$R^{18}$ is independently hydrogen or a $C_1$-$C_{10}$ alkyl group;
each q is independently an integer selected from the range of 1 to 10.

In an embodiment, the first reagent comprises a monomer represented by the formula

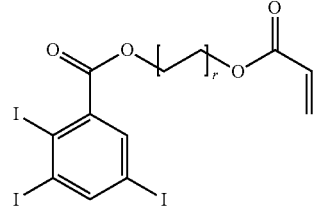

Formula 1-D where r is an integer from 2 to 36. In different embodiments, r is from 6 to 12, 6-16 or from 8 to 20. The first reagent may also comprise a first iodinated monomer represented by Formula 1-D with a first value of r and a second iodinated monomer represented by Formula 1-D with a second value of r different than the first. In an embodiment, the average number of iodine atoms is 3 for a monomer represented by Formula 1-D, but the monomer may also include components with smaller numbers of iodine atoms.

In an aspect, the crosslinking monomer or oligomer comprises a central portion and at least two end portions, at least one of the end portions being branched. In an embodiment, the crosslinking monomer may be represented by $$Y^1\text{-}L^1\text{-}R^1\text{-}L^1\text{-}Y^2 \qquad \text{(Formula 2)}$$

wherein $R^1$ is the central portion, $Y^1$ and $Y^2$ are end portions, and $L^1$ is a linking moiety.

In an embodiment, the central portion $R^1$ in Formula 2 is substituted or unsubstituted $C_2$-$C_{36}$ alkylene, $C_3$-$C_{36}$ cycloalkylene, $C_2$-$C_{36}$ alkenylene, $C_3$-$C_{36}$ cycloalkenylene, $C_2$-$C_{36}$ alkynylene, $C_5$-$C_{36}$ arylene, $C_5$-$C_{36}$ heteroarylene, an oligomeric polyether, Formula 3, an oligomeric polycarbonate, Formula 4, an oligomeric polyurethane, Formula 5, wherein Formula 3, 4 and 5 are

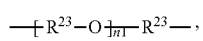

Formula 3

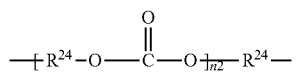

Formula 4

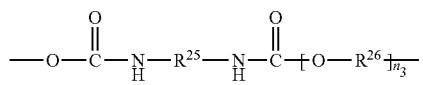

Formula 5

And wherein $R^{23}$ in Formula 3 is $C_4$-$C_{20}$ alkylene and n1 is an integer from 1 to 50, $R^{24}$ in Formula 4 is $C_3$-$C_{20}$ alkylene and n2 is an integer from 1 to 50, $R^{25}$ in Formula 5 is aliphatic group, substituted or unsubstituted $C_2$-$C_{36}$ alkylene, $C_3$-$C_{36}$ cycloalkylene, $C_2$-$C_{36}$ alkenylene, $C_3$-$C_{36}$ cycloalkenylene, $C_2$-$C_{36}$ alkynylene, $C_5$-$C_{36}$ arylene, $C_5$-$C_{36}$ heteroarylene, aromatic group, polyalkyl siloxane group, polyether group, polyester group, polycarbonate group or a combination of linear or branched aliphatic groups and aromatic groups, $R^{26}$ in Formula 5 is aliphatic group, substituted or unsubstituted $C_2$-$C_{36}$ alkylene, $C_3$-$C_{36}$ cycloalkylene, $C_2$-$C_{36}$ alkenylene, $C_3$-$C_{36}$ cycloalkenylene, $C_2$-$C_{36}$ alkynylene, $C_5$-$C_{36}$ arylene, $C_5$-$C_{36}$ heteroarylene, aromatic group, polyalkyl siloxane group, polyether group, polyester group, polycarbonate group or a combination of linear or branched aliphatic groups and aromatic groups and n3 is an integer from 1 to 50.

In an embodiment, $Y^1$ and/or $Y^2$ in Formula 2 is represented by (where the bond with the wavy line across it indicates connection to another part of the molecule):

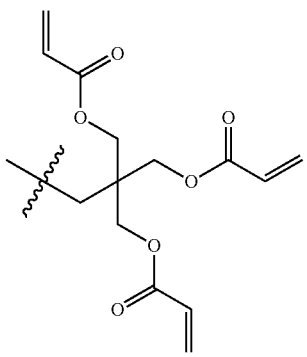

Formula 20

In another embodiment, $Y^1$ and/or $Y^2$ is represented by:

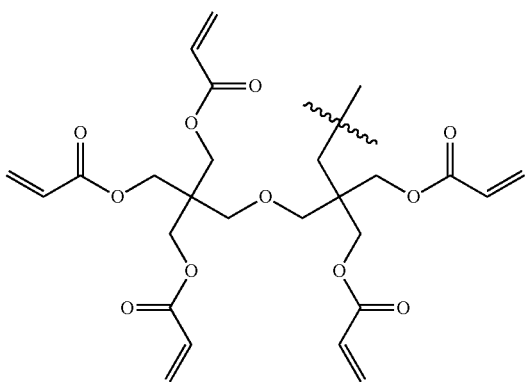

Formula 21

In an embodiment, $L^1$ in Formula 2 is a single bond, —(CH$_2$)$_n$—, —(HCCH)$_n$—, —O—, —S—, —SO—, —SO$_2$—, —SO$_3$—, —OSO$_2$—, —NR$^3$—, —CO—, —COO—, —OCO—, —OCOO—, —CONR$^4$—, —NR$^5$CO—, —OCONR$^6$—, —NR$^7$COO—, or —NR$^8$CONR$^9$— and each of $R^3$-$R^9$ is independently hydrogen or $C_1$-$C_{10}$ alkyl;

In an embodiment, one of $Y^1$ and $Y^2$ is according to Formula 20 or 21 and the other of $Y^1$ and $Y^2$ is selected from the group consisting of —COCl, —COH, —COR$^{19}$, —CONR$^{20}$R$^{21}$, $R^{19}$ is a $C_1$-$C_{10}$ alkyl group and each of $R^{20}$-$R^{21}$ is independently hydrogen or a $C_1$-$C_{10}$ alkyl group.

In an aspect, the second reagent comprises a crosslinker reagent represented by the formula:

(Formula 2-A)

where p is 2 or 3;
each n is independently an integer from 1 to 3 with p*n≥3;
each X in Formula 2-A is independently a single bond, —CH$_q$— where q is (3−n); or X is —N—;
$R^1$ is a substituted or unsubstituted $C_2$-$C_{36}$ alkylene group; $C_3$-$C_{36}$ cycloalkylene group; $C_2$-$C_{36}$ alkenylene group; $C_3$-$C_{36}$ cycloalkenylene group; $C_2$-$C_{36}$ alkynylene group; $C_5$-$C_{36}$ arylene group having from one to three rings; or $C_5$-$C_{36}$ heteroarylene group;
each $L^2$ is independently a single bond; —(CH$_2$)$_m$—; —(HCCH)$_m$—; —O—; —(CH$_2$)$_m$—O—; —O—(CH$_2$)$_m$—;

—S—; —SO—; —SO$_2$—; —SO$_3$—; —OSO$_2$—; —NR$^3$—; —(CH$_2$)$_m$—NR$^3$—; —NR$^3$—(CH$_2$)$_m$—; —CO—; —(CH$_2$)$_m$—CO—; —CO—(CH$_2$)$_m$—; —COO—; —COO—(CH$_2$)$_m$—; —(CH$_2$)$_m$—COO—; —OCO—; —(CH$_2$)$_m$—OCO—; —OCO—(CH$_2$)$_m$—; —(CH$_2$)$_m$OCOO—; —OCOO—(CH$_2$)$_m$—; OCOO—; —CONR$^4$—, —NR$^5$CO—, —OCONR$^6$—, —NR$^7$COO—, —(CH$_2$)$_m$—NR$^7$COO—, —NR$^7$COO—(CH$_2$)$_m$—; —NR$^8$CONR$^9$—; each R$^2$ is independently

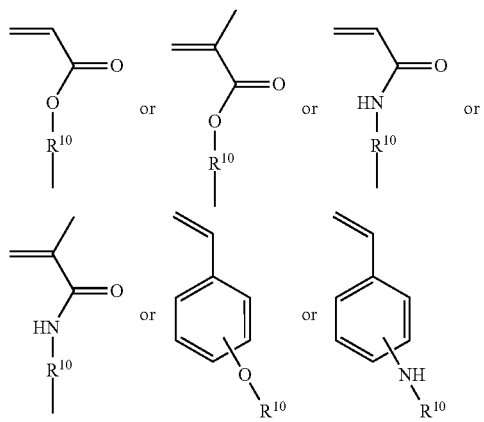

where each R$^{10}$ is independently a single bond; substituted or unsubstituted C$_1$-C$_{36}$ alkylene group; C$_3$-C$_{36}$ cycloalkylene group; C$_2$-C$_{36}$ alkenylene group; C$_3$-C$_{36}$ cycloalkenylene group; C$_2$-C$_{36}$ alkynylene group; C$_5$-C$_{36}$ arylene group; or C$_5$-C$_{36}$ heteroarylene group.

In an embodiment, the invention provides polymer compositions comprising a repeating unit derived from Formula 1, Formula 1-A, Formula 1-B or Formula 1-C, wherein L$^{11}$ is a single bond, thereby providing direct linking between R$^{11}$ and Ar$^{11}$ via a single bond.

In an embodiment, in the crosslinker monomer or oligomer of Formula 2-A, p is 2 and n is 3. In an embodiment, in the formulas above (e.g. Formulas 2 and 2-A), R$^1$ is a C$_2$-C$_{10}$ alkylene group, C$_6$-C$_{20}$ alkylene group or C6-C16 alkylene. In an embodiment, in the formulas above, R$^2$ is —(CH$_2$)$_t$—O—CO—CH=CH$_2$, where t is an integer from 1 to 6. In an embodiment, in the formulas above, R$^1$ is one or more aryl ring groups. In an embodiment, in the formulas above, the crosslinker monomer has the formula:

Formula 2-B

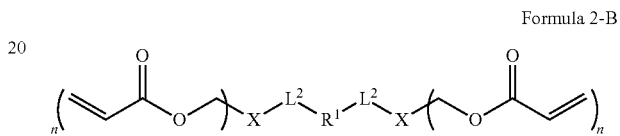

where the variables are as defined above for Formula 2-A and n is 2 or 3. In an embodiment, in the formulas above, L$^2$ is selected from the group consisting of: —NH—CO—O—(CH$_2$)$_u$—; —CO—O—(CH$_2$)$_u$—; where each u is independently an integer from 1 to 6

In an embodiment, the crosslinker monomer is selected from one or more of the following:

(Formula 6-A)

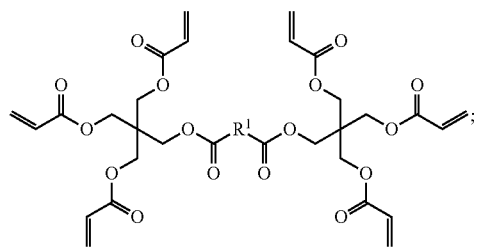

(Formula 6-B)

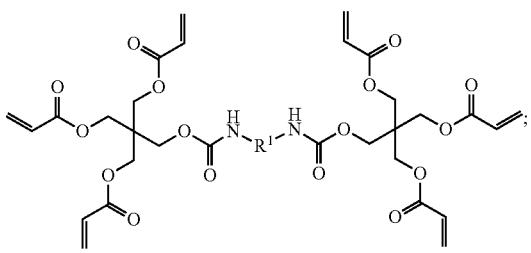

(Formula 6-C)

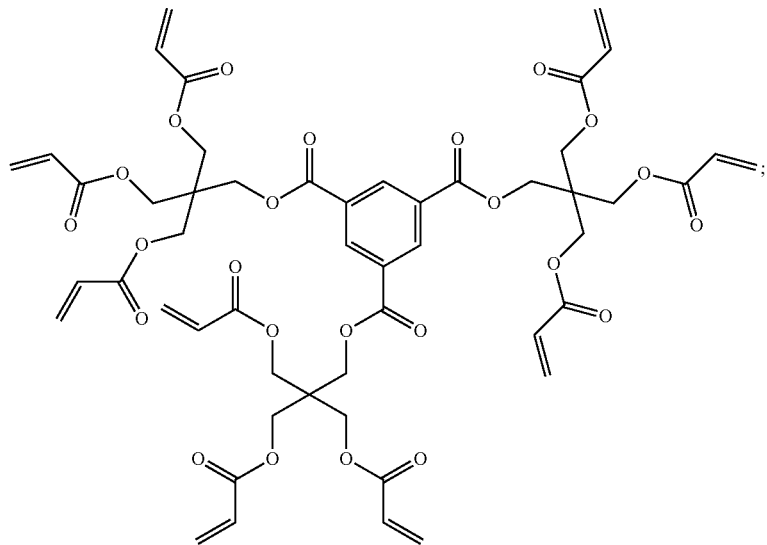

(Formula 6-D)
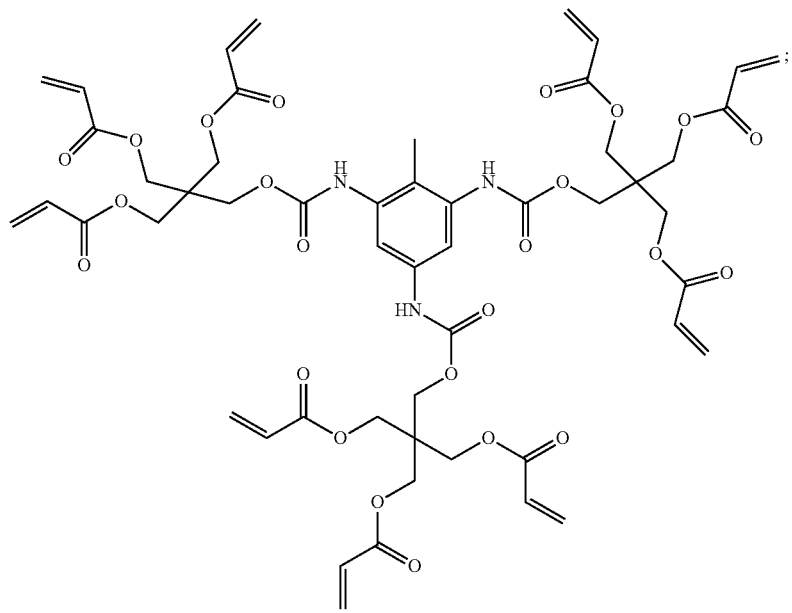
(Formula 6-E)
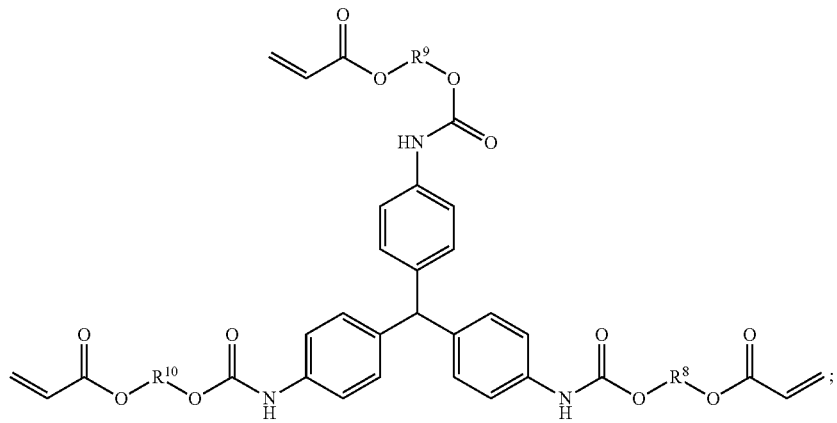
(Formula 6-F)
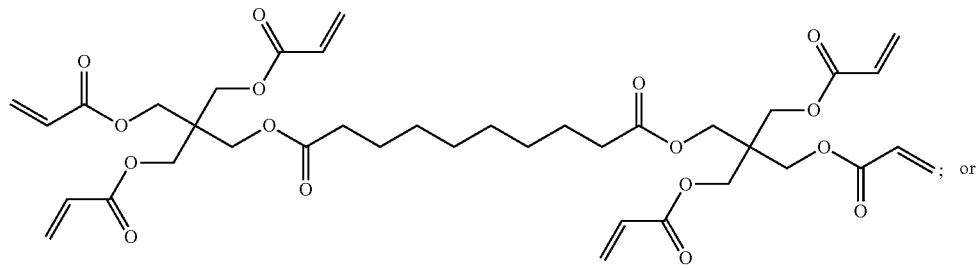
; or
(Formula 6-G)
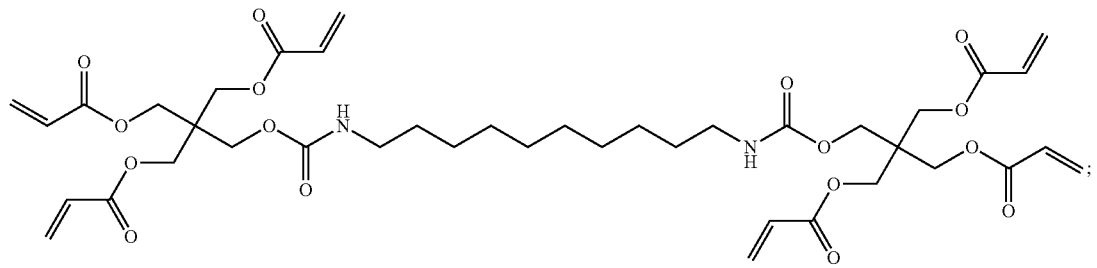
;

In Formula 6-E, $R^8$, $R^9$ and $R^{10}$ can each be a substituted or unsubstituted $C_2$-$C_{36}$ alkylene, $C_3$-$C_{36}$ cycloalkylene, $C_2$-$C_{36}$ alkenylene, $C_3$-$C_{36}$ cycloalkenylene, $C_2$-$C_{36}$ alkynylene, $C_5$-$C_{36}$ arylene, $C_5$-$C_{36}$ heteroarylene, an oligomeric polyether, (Formula 3) an oligomeric polycarbonate (Formula 4), or an oligomeric polyurethane (Formula 5), and furthermore $R^8$, $R^9$ and $R^{10}$ can be such that all three are the same, two of them can be the same and one different, or all three can be different. $R^1$ may be defined as for formula 2-A.

In another embodiment, an additional crosslinking monomer or oligomer comprising a terminal group other than a polymerizable group may be used in combination with the monomer or oligomer represented by Formula 2-A. In an embodiment, the additional crosslinking monomer or oligomer may be represented by Formula 2-C below.

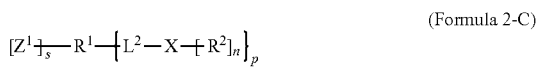
(Formula 2-C)

Where $R^1$, $L^2$, X and $R^2$ are as described for formula 2-A above and, $Z^1$ is —COCl, —COH—, —COR$^{19}$, —CONR$^{20}$R$^{21}$, $R^{19}$ is a $C_1$-$C_{10}$ alkyl group and each of $R^{20}$-$R^{21}$ is independently hydrogen or a $C_1$-$C_{10}$ alkyl group, p is 1, 2 or 3; each n is independently an integer from 1 to 3 with p*n≥3 and s is an integer from 1 to 2;

In another embodiment, an additional crosslinking monomer may be used in combination with the monomer represented by Formula 2-B. Such an additional crosslinking monomer may be represented by the formula

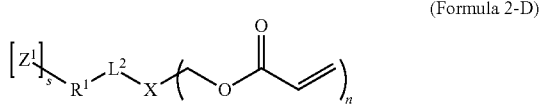
(Formula 2-D)

where n is 2 or 3, s, X, W and C are as described for formula 2-A above and $Z^1$ is —COCl, —COH, —COR$^{19}$, —CONR$^{20}$R$^{21}$, where $R^{19}$ is a $C_1$-$C_{10}$ alkyl group and each of $R^{20}$-$R^{21}$ is independently hydrogen or a $C_1$-$C_{10}$ alkyl group. In an embodiment, in formula 2-D $R^1$ is a $C_2$-$C_{10}$ alkylene group, C6C20 alkylene group or C6-C16 aklyene group and s is one in Formula 2-D. In another embodiment, $R^1$ is an aryl ring group and s is 1 or 2. In an embodiment, in formula 2-D above $L^1$ is selected from the group consisting of: —NH—CO—O—(CH$_2$)$_u$—; —CO—O—(CH$_2$)$_u$; where each u is independently an integer from 1 to 6.

In another embodiment, the additional crosslinking monomer may also be a branched multifunctional monomer. In an embodiment, the additional crosslinking monomer may be dipentaerythritol pentaacrylate ([2-(hydroxymethyl)-3-prop-2-enoyloxy-2-[[3-prop-2-enoyloxy-2,2-bis(prop-2-enoyloxymethyl)propoxy]methyl]propyl]prop-2-enoate), dipentaerythritol hexaacrylate; dipentaerythritol triacrylate; dipentaerythritol tetraacylate.

In an embodiment, provided is a polymer composition obtained by the polymerization reaction of: a) a first reagent comprising one or more first monomers selected from the group consisting of Formula 1, Formula 1-A, Formula 1-B and Formula 1-C and b) a second reagent comprising one or more crosslinker monomers or oligomers, wherein the one or more first monomers are collectively present in the composition at between 60 and 99 wt % and the one or more crosslinker monomers or oligomers is present in the composition between 1 and 40 wt %. In other embodiments, the one or more first monomers are collectively present in the composition at from 60 to 90 wt %, 70 and 90 wt % or 75 and 85 wt % and the one or more crosslinker monomers or oligomers are collectively present in the composition a from 40 to 10 wt %, t between 30 and 10% or between 25 and 15 wt %. In an embodiment, the polymer is a shape memory polymer.

In an embodiment, provided is a polymer composition obtained by the polymerization reaction of: a) one or more first monomers selected from the group consisting of Formula 1, Formula 1-A, Formula 1-B and Formula 1-C and one or more crosslinker monomers or oligomers, further comprising a second crosslinker monomer represented by Formula 14:

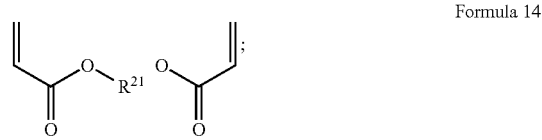
Formula 14 wherein $R^{21}$ is a substituted or unsubstituted $C_2$-$C_{36}$ alkylene group; $C_3$-$C_{36}$ cycloalkylene group; $C_2$-$C_{36}$ alkenylene group; $C_3$-$C_{36}$ cycloalkenylene group; $C_2$-$C_{36}$ alkynylene group; $C_6$-$C_{36}$ arylene group; $C_6$-$C_{36}$ heteroarylene group; Formula 3; Formula 4 or Formula 5;

(Formula 3)

where in Formula 3, each $R^{23}$ is independently a C4-C20 alkylene group and each n1 is independently an integer from 1 to 50;

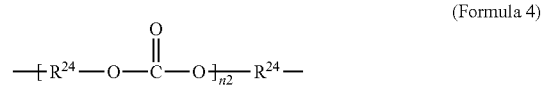
(Formula 4)

where in Formula 4, each $R^{24}$ is independently a C3-C20 alkylene group and each n2 is independently an integer from 1 to 50;

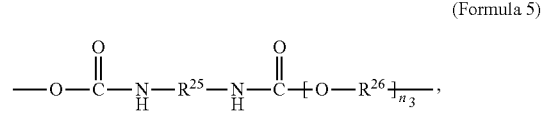
(Formula 5)

where in Formula 5, each $R^{25}$ and each $R^{26}$ is independently an aliphatic group; aromatic group; polyalkyl siloxane group; polyether group; polyester group; polycarbonate group or a combination of linear or branched aliphatic groups and aromatic groups; and each n3 is independently an integer from 1 to 50. In an embodiment, in a first monomer, $L^{11}$ is an ester or amide group. In an embodiment, a crosslinker monomer is non-iodinated. In an embodiment, in the formulas above, when $Ar^{11}$ contains iodine, the concentration of iodine in the polymer composition is at least 200 mg/mm$^3$. In an embodiment, in the formulas above, $Ar^{11}$ is an iodinated $C_5$-$C_{36}$ aryl group or $C_5$-$C_{36}$ heteroaryl group.

In an aspect, the crosslinker monomer or oligomer is hyperbranched. As used herein, a hyperbranched molecule includes branches upon branches. In an embodiment, the degree of branching of the crosslinker is from 0.25 to 0.50. In different embodiments, the crosslinker comprises from 3 to 20, from 6 to 20 or from 8 to 20 terminal acrylate groups. In an embodiment, the hyperbranched polymer is a hyperbranched polyester monomer comprising terminal acrylate groups. Suitable hyperbranched polyester monomers include, but are not limited to CN2300 (acrylate functionality=8), CN2301 (acrylate functionality=9), CN2302 (acrylate functionality=16), CN2303 (acrylate functionality=6) and CN2304 (acrylate functionality=18) all available from Sartomer®. Also provided is a method of making a crosslinked polymer composition the steps of forming a precursor mixture comprising a first reagent comprising one or more monomers including iondine, bromine or bismuth and a second reagent comprising a crosslinking reagent, where the first and second reagent are as described above, and polymerizing with an initiator.

In an embodiment, provided is a radiopaque polymer device for medical applications, the device or a device feature comprising a polymer composition according to the description herein. In an embodiment, the polymer is a shape memory polymer having a glass transition temperature (Tg) between 25° C. to 50° C. and a rubbery modulus between 0.1 MPa and 15 MPa at 37° C. In an embodiment, the polymer exhibits a glass transition temperature (Tg) and a Tan Delta (Loss Modulus/Storage Modulus ratio) curve related to temperature; the polymer's maximum rate of shape change occurs at an environmental operating temperature (To) that is coincident with the temperature at which the material's Tan Delta value is ≤60% of its peak value, above Tg. In an embodiment, a device described herein is useful for purposes of an indwelling, permanent implant to provide the function of:
  a. opening, or maintaining an open anatomical lumen;
  b. closing an anatomical lumen, either partially as a valve, or complete lumen occlusion for any physiological fluid or gas flow or for a applied therapeutic fluid or gas flow;
  c. support of an anatomical structure to assist in therapeutic restoration of an organ, vascular, digestive, excrement, or airway function;
  d. support of an anatomical structure to assist in therapeutic restoration of an orthopaedic, maxiofacial, spinal, joint or other skeletal or function; or
  e. to support hemostasis by covering an area after tissue dissection or resection, a patch, such as for hemostasis of the liver, or other organ.

In an embodiment, a device described herein is useful for purposes of a diagnostic or therapeutic instrument or device to provide the function of:
  a. a catheter for the purposes of accessing an anatomical location; delivering another device and/or therapeutic agent; or controlling the access or delivery of another device and/or therapeutic agent; or
  b. a temporarily indwelling device to provide a limited time therapeutic benefit, such as a vena cava filter that is placed in a vessel, left indwelling for a period of time, for example to capture blood clots, and subsequently removed when the therapeutic period is completed.

In an embodiment, the polymers of the invention do not contain any metal materials or metal components or elements but still exhibit suitable radiopacity for clinical viewing using conventional imaging systems. Clinicians are commonly challenged by obscuring artifacts from metal and metal based implanted devices when attempting to image using either CT scan (Computed Tomography) or MRI (Magnetic Resonance Imaging). The significance of the artifact is typically based upon the amount of metal content and can be so excessive as to inhibit the ability to clinically image the device. This situation can require an alternative means to clinically evaluate the patient or device (e.g. angiogram, etc.) which may not only be more costly, but more invasive and risky to the patient. As such, a non-metallic, radiopaque polymer reflects a significant advantage and differentiation from other approaches for radiopaque devices. In an embodiment, a material or device disclosed herein contains metal. In one aspect, a device disclosed contains metal in the form of marker bands, as conventionally used for visualization. In one aspect, the devices disclosed comprise platinum-iridium or gold marker bands, as known in the art. As known in the art, "marker bands" may be used to achieve a specific product requirement, such as demarcation of an edge of the device or alignment of two devices for proper use, for example. The use of marker bands is optional with the materials and devices described here.

The compositions and compounds disclosed include a radiopaque functionality. In an aspect, the radiopaque functionality is one or more iodine atoms. In an aspect, the radiopaque functionality is one or more Br or Bi atoms. In an embodiment, the compositions and compounds of the invention include covalently bound heavy atoms such as iodine. In this embodiment, the distribution of iodine or other radiopaque functionality within the polymer is sufficiently homogeneous so as to be efficacious for imaging applications. In different embodiments, the polymer composition may include repeating units derived from one or more monofunctional iodinated and/or non-iodinated co-monomers and/or one or more multifunctional crosslinker monomers or oligomers.

In an embodiment, the polymers of the present invention are sufficiently amorphous that some conventional analysis methods do not indicate the presence of residual amounts of crystallinity. In an embodiment, the polymers described herein are not sufficiently crystalline as to cause devices incorporating the polymers to be inoperative in the desired uses. In general, if shape memory polymers are semicrystalline, shape change can be hindered and slowed, and device performance can become clinically undesirable. The crystallinity of the shape memory polymer and non-shape memory polymers described here can be affected by the selection of the components used to form the polymer, as further described herein.

In an embodiment, the glass transition temperature and rubbery modulus of the polymers of the present invention can be adjusted independently, as further described herein.

In an embodiment, the invention provides a polymer which has sufficient resistance to water absorption that it can be used to fabricate medical devices or device components for use in a physiological environment with exposure to body fluid(s). In an embodiment, the medical devices or device components show little change in their mechanical properties or degradation of their mechanical integrity during the useful lifetime of the device. In an embodiment, the devices and compositions described here are useful for permanent (or long-term) implantation or use in a biological system. In an embodiment, devices or device components formed using the polymer compositions of the invention exhibit a water uptake of less than 1.0% by weight over a 24 hour period. In an embodiment, devices or device components formed using the polymer compositions of the invention exhibit a water uptake of less than 0.5% by weight over a 24 hour period.

In one embodiment, none of the components of the polymer composition is fluorinated. In an embodiment, the polymer composition does not include poly(ethylene glycol) di(meth)acrylate (PEGDA or PEGDMA).

In an aspect, provided is a polymer composition comprising a crosslinked polymer network. The crosslinked polymer network comprises the result of a polymerization reaction of a first reagent comprising one or more monomers and a second reagent comprising one or more crosslinker monomers or oligomers, where at least one of the crosslinker monomers or oligomers has more than two polymerizable groups. As used herein, a "polymerizable group" is a group that is available for a polymerization reaction. Examples of polymerizable groups, not intending to limit the scope, include ethylene groups, acrylate groups, methacrylate groups, acrylamide groups, methacrylamide groups, and styryl groups.

In an embodiment, the crosslinked network is characterized by covalent bonding between a first monomer and a crosslinker monomer or oligomer such that the crosslinker monomer or oligomer forms the crosslinking of the crosslinked network.

In an embodiment, the first reagent comprises a first monomer which is iodinated. In an embodiment, an iodinated first monomer contains an average of between 1 to 4 iodine atoms per repeating unit. In an embodiment, a first monomer is an acrylate ester of 2,3,5-triiodobenzoic acid. A multifunctional crosslinker monomer or oligomer may have two or more polymerizable functional groups, such as acrylate groups. In different embodiments, the polymer composition may include repeating units derived from one or more monofunctional iodinated and/or non-iodinated co-monomers and one or more multifunctional crosslinker monomers or oligomers, wherein at least one of the multifunctional crosslinker monomers or oligomers has at least three polymerizable functional groups. In different embodiments, there is more than one crosslinker monomer or oligomer used in the compounds and compositions provided. In an embodiment, a crosslinker monomer or oligomer has a polymer backbone that causes the structure to have the characteristics of an elastomer, a reinforced plastic, or any other polymer backbone capable of producing a desirable functional outcome for the final crosslinked product. In an embodiment, a crosslinker monomer or oligomer is multifunctional with more than two polymerizable groups. In an embodiment, there is more than one crosslinker monomer or oligomer in the composition, where one crosslinker monomer or oligomer is multifunctional with more than two polymerizable groups.

Use of monomers or oligomers with different chemical structures and amounts thereof can be used to suppress formation of crystalline regions in the polymer compositions of the invention. In an embodiment, the monomers or oligomers are selected for phase compatibility in the liquid and solid state. Phase compatibility of the monomers or oligomers can facilitate random incorporation of the monomer or oligomer units during free radical polymerization and homogeneity in the resulting polymer.

The polymer precursor mixture may comprise more than one monomer comprising iodine, bromine or bismuth and more than one crosslinker monomer or oligomer. In an embodiment, one of the crosslinker monomers or oligomers may be of higher molecular weight than the other(s). In an embodiment, one of the crosslinker monomers or oligomers has a molecular weight greater than or equal to 250 and less than or equal to 1000 and the other has a molecular weight greater than 1000 and less than 5000. In an embodiment, one of the crosslinker molecules has a molecular weight greater than or equal to 500 and less than or equal to 1000 and the other has a molecular weight greater than or equal to 1500 and less than or equal to 3000. In an embodiment, one of the crosslinker monomers or oligomers may have a molecular weight greater than or equal to 200 and less than 500 while the other may have a molecular weight greater than or equal to 500 and less than or equal to 1000.

In an embodiment, the amount of the crosslinker monomer or oligomer is as low as possible and still results in a polymer that functions as desired. In other words, the iodinated monomer is as high as possible in the compositions described here. In an embodiment, the total wt % of the crosslinker reagent is from 20 wt % to as low as can be incorporated and crosslink. In an embodiment, the total wt % of the crosslinker reagent is from 20 wt % to 0.001 wt %. In an embodiment, the total wt % of the crosslinker reagent is from 20 wt % to 1 wt %. In an embodiment, the total wt % of the crosslinker reagent is from 5 wt % to 1 wt %. In an embodiment, the total wt % of the crosslinker reagent is from 10 wt % to 1 wt %. In an embodiment, the total wt % of the crosslinker reagent is from 5 to 35 wt %, from 10 to 30 wt % or from 15 to 25 wt %. All intermediate ranges and individual values of crosslinker reagent and other components are intended to be included to the extent as if they were individually mentioned for any purpose, including incorporation in a claim or creation of a range or intermediate range.

In an embodiment, when there is more than one crosslinker monomer in a composition, the weight percentage of the higher molecular weight crosslinker monomer is from 0-20 wt % while the weight percentage of the lower molecular weight crosslinker monomer is from 0-20 wt %, and all other permutations yielding a useful composition for the intended use.

In another aspect, the invention provides radiopaque medical devices. The original molded shape of radiopaque medical devices of the present invention can be deformed into a temporary shape typically having a reduced profile to facilitate insertion into a vessel, lumen, or other aperture or cavity. After insertion, the device can self-expand to assume a deployed configuration. In an embodiment, the medical device may assume its deployed configuration due to changes in temperature or other stimuli. In an embodiment, these SMP devices are capable of exhibiting shape memory behavior at physiological temperatures and may be used in surgical and catheter based procedures. In an embodiment, the medical device's deployed configuration may have one or more useful purposes including lumen occlusion, lumen opening or stenting, device anchoring or retention, patching or sealing a surface, structural restoration or localized drug delivery. The devices may use a SMP property of the compound or composition or may not use this property, if found in the compound or composition.

In an embodiment, the glass transition temperature of the polymer may be up to 50° C. In an embodiment, the glass transition temperature of the polymer is up to 75° C., though any other polymer glass transition temperature that produces a useful final product is intended to be included as well. In an embodiment the glass transition temperature is as far below room temperature as possible so that a shape memory polymer shape (coil, for example) is elastic with a fast enough shape recovery for use in a desired application. This temperature and useable shape recovery speed can be easily determined by one of ordinary skill in the art. In some embodiments, the glass transition temperature may be suppressed below body temperature. When a polymer formed from such a device is delivered in a catheter or other delivery device, the material may already transition to its rubbery state in the delivery device. This can allow achievement of a more rapid response (elastic response) from the device after delivery (e.g. in the vessel).

As used herein, the term "group" may refer to a functional group of a chemical compound. Groups of the present compounds refer to an atom or a collection of atoms that are a part of the compound. Groups of the present invention may be attached to other atoms of the compound via one or more covalent bonds. Groups may also be characterized with respect to their valence state. The present invention includes groups characterized as monovalent, divalent, trivalent, etc. valence states.

As used throughout the present description, the expression "a group corresponding to" an indicated species expressly includes a moiety derived from the group including a monovalent, divalent or trivalent group.

As is customary and well known in the art, hydrogen atoms in the Formulas included are not always explicitly shown, for example, hydrogen atoms bonded to the carbon atoms of the polymer backbone, crosslinker groups, aromatic group, etc. The structures provided herein, for example in the context of the description of the Formulas, are intended to convey to one of reasonable skill in the art the chemical composition of compounds of the methods and compositions of the invention, and as will be understood by one of skill in the art, the structures provided do not indicate the specific positions of atoms and bond angles between atoms of these compounds.

As used herein, the terms "alkylene" and "alkylene group" are used synonymously and refer to a divalent group derived from an alkyl group as defined herein. The invention includes compounds having one or more alkylene groups. Alkylene groups in some compounds function as attaching and/or spacer groups. Compounds of the invention may have substituted and/or unsubstituted $C_1$-$C_{20}$ alkylene, $C_1$-$C_{10}$ alkylene and $C_1$-$C_5$ alkylene groups.

As used herein, the term "halo" refers to a halogen group such as a fluoro (—F), chloro (—Cl), bromo (—Br), iodo (—I) or astato (—At).

Alkyl groups include straight-chain, branched and cyclic alkyl groups. Alkyl groups include those having from 1 to 30 carbon atoms. Alkyl groups include small alkyl groups having 1 to 3 carbon atoms. Alkyl groups include medium length alkyl groups having from 4-10 carbon atoms. Alkyl groups include long alkyl groups having more than 10 carbon atoms, particularly those having 10-30 carbon atoms. The term cycloalkyl specifically refers to an alky group having a ring structure such as ring structure comprising 3-30 carbon atoms, optionally 3-20 carbon atoms and optionally 2-10 carbon atoms, including an alkyl group having one or more rings. Cycloalkyl groups include those having a 3-, 4-, 5-, 6-, 7-, 8-, 9- or 10-member carbon ring(s) and particularly those having a 3-, 4-, 5-, 6-, or 7-member ring(s). The carbon rings in cycloalkyl groups can also carry alkyl groups. Cycloalkyl groups can include bicyclic and tricycloalkyl groups. Alkyl groups are optionally substituted. Substituted alkyl groups include among others those which are substituted with aryl groups, which in turn can be optionally substituted. Specific alkyl groups include methyl, ethyl, n-propyl, iso-propyl, cyclopropyl, n-butyl, s-butyl, t-butyl, cyclobutyl, n-pentyl, branched-pentyl, cyclopentyl, n-hexyl, branched hexyl, and cyclohexyl groups, all of which are optionally substituted. Substituted alkyl groups include fully halogenated or semihalogenated alkyl groups, such as alkyl groups having one or more hydrogens replaced with one or more fluorine atoms, chlorine atoms, bromine atoms and/or iodine atoms. Substituted alkyl groups include fully fluorinated or semifluorinated alkyl groups, such as alkyl groups having one or more hydrogens replaced with one or more fluorine atoms. An alkoxy group is an alkyl group that has been modified by linkage to oxygen and can be represented by the formula R—O and can also be referred to as an alkyl ether group. Examples of alkoxy groups include, but are not limited to, methoxy, ethoxy, propoxy, butoxy and heptoxy. Alkoxy groups include substituted alkoxy groups wherein the alky portion of the groups is substituted as provided herein in connection with the description of alkyl groups. As used herein MeO— refers to $CH_3O$—.

Aryl groups include groups having one or more 5-, 6- or 7-member aromatic and/or heterocyclic aromatic rings. The term heteroaryl specifically refers to aryl groups having at least one 5-, 6- or 7-member heterocyclic aromatic rings. Aryl groups can contain one or more fused aromatic and heteroaromatic rings or a combination of one or more aromatic or heteroaromatic rings and one or more non-aromatic rings that may be fused or linked via covalent bonds. Heterocyclic aromatic rings can include one or more N, O, or S atoms in the ring. Heterocyclic aromatic rings can include those with one, two or three N atoms, those with one or two 0 atoms, and those with one or two S atoms, or combinations of one or two or three N, O or S atoms. Aryl groups are optionally substituted. Substituted aryl groups include among others those which are substituted with alkyl or alkenyl groups, which groups in turn can be optionally substituted. Specific aryl groups include phenyl, biphenyl groups, pyrrolidinyl, imidazolidinyl, tetrahydrofuryl, tetrahydrothienyl, furyl, thienyl, pyridyl, quinolyl, isoquinolyl, pyridazinyl, pyrazinyl, indolyl, imidazolyl, oxazolyl, thiazolyl, pyrazolyl, pyridinyl, benzoxadiazolyl, benzothiadiazolyl, and naphthyl groups, all of which are optionally substituted. Substituted aryl groups include fully halogenated or semihalogenated aryl groups, such as aryl groups having one or more hydrogens replaced with one or more fluorine atoms, chlorine atoms, bromine atoms and/or iodine atoms. Substituted aryl groups include fully fluorinated or semifluorinated aryl groups, such as aryl groups having one or more hydrogens replaced with one or more fluorine atoms. Aryl groups include, but are not limited to, aromatic group-containing or heterocylic aromatic group-containing groups corresponding to any one of the following: benzene, naphthalene, naphthoquinone, diphenylmethane, fluorene, anthracene, anthraquinone, phenanthrene, tetracene, tetracenedione, pyridine, quinoline, isoquinoline, indoles, isoindole, pyrrole, imidazole, oxazole, thiazole, pyrazole, pyrazine, pyrimidine, purine, benzimidazole, furans, benzofuran, dibenzofuran, carbazole, acridine, acridone, phenanthridine, thiophene, benzothiophene, dibenzothiophene, xanthene, xanthone, flavone, coumarin, azulene or anthracycline. As used herein, a group corresponding to the groups listed above expressly includes an aromatic or heterocyclic aromatic group, including monovalent, divalent and polyvalent groups, of the aromatic and heterocyclic aromatic groups listed herein are provided in a covalently bonded configuration in the compounds of the invention at any suitable point of attachment. In embodiments, aryl groups contain between 5 and 30 carbon atoms. In embodiments, aryl groups contain one aromatic or heteroaromatic six-membered ring and one or more additional five- or six-membered aromatic or heteroaromatic ring. In embodiments, aryl groups contain between five and eighteen carbon atoms in the rings. Aryl groups optionally have one or more aromatic rings or heterocyclic aromatic rings having one or more electron donating groups, electron withdrawing groups and/or targeting ligands provided as substituents.

DETAILED DESCRIPTION OF THE INVENTION

Figure 1:
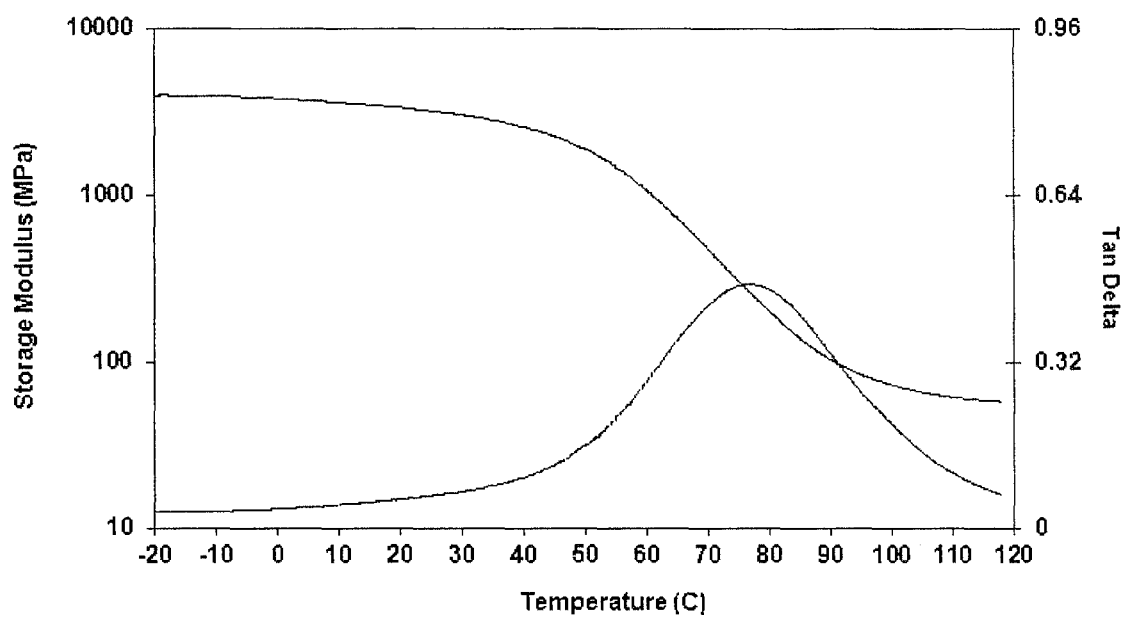
FIG. 1 shows Dynamic Mechanical Analysis (DMA) properties of the material comprised of 67% of the iodinated monomer represented by Formula 1 in which $R^{11}$ is an ethyl ($C_2$) spacer group, $L^{11}$ is an ester connecting group, and $Ar^{11}$ is a 2,3,5-triiodobenzoate group, and 33% of the clustered crosslinker described in Example 2.

As used herein, a crosslinked network is a polymer composition comprising a plurality of polymer chains wherein a large portion (e.g., 80%) and optionally all the polymer chains are interconnected, for example via covalent crosslinking, to form a single polymer composition. In an embodiment, the invention provides a radiopaque polymer in the form of a crosslinked network in which at least some of the crosslinks of the network structure are formed by covalent bonds. Radiopacity refers to the relative inability of electromagnetism, particularly X-rays, to pass through dense materials. The two main factors contributing to a material's radiopacity are density and atomic number of the radiopaque element. In an embodiment, this invention utilizes incorporated (trapped) iodine molecules within the polymer matrix to induce radiopaque functionality. In an embodiment, the radiopaque polymer is an iodinated polymer. As referred to herein, iodinated polymers are produced by incorporating (trapping) iodine molecules on a select monomer prior to formulation of the monomer into a polymer. Although iodine is used in some examples and descriptions herein, it is recognized that other radiopaque materials may be used, such as Bi and Br and that the descriptions here apply to and may be used with other radiopaque materials.

As referred to herein, a monomer or monomer reagent is a reagent which can undergo polymerization under appropriate conditions. A monomer reagent comprises at least one monomer molecule, where a monomer molecule is a molecule which can undergo polymerization, thereby contributing constitutional units to the structure of a macromolecule or oligomer. In an embodiment, a monomer reagent may be represented by an average or dominant chemical structure and comprise monomer molecules having that chemical structure but may also contain components with other chemical structures. For example, a monomer reagent may comprise impurities having chemical structures other than the average or dominant structure of the reagent. An oligomer or oligomeric reagent is also a reagent which can undergo polymerization under appropriate conditions. An oligomeric reagent comprises an oligomer molecule, the oligomer molecule comprising a small plurality of units derived from molecules of lower relative molecular mass. In an embodiment, certain hyperbranched crosslinking reagents suitable for use with the invention may be regarded as oligomeric reagents.

As is known in the art, the chemical structures of the compositions shown are intended to be representation of average or dominant structures. In an embodiment, a monomer or oligomer reagent may be represented by an average or dominant chemical structure and comprise components having that chemical structure, but may also contain components with other chemical structures. For example, when a monomer or oligomer reagent functionalized with polymerizable groups is formed through reaction of a first component with a second component comprising polymerizable groups, the resulting product may vary due to impurities present in the two components and/or due to variation in the extent of reaction between the two components. In an embodiment, extent of reaction between the two components is limited so that at least some of the reaction products include less than the maximum number of possible polymerizable groups. In an embodiment, for example, all structures involving the pentaerythritol triacrylate appendages are average structures.

In an embodiment, the iodinated crosslinked polymers of the invention are formed by the polymerization of a polymer precursor mixture comprising an iodinated monofunctional monomer, a multifunctional crosslinker monomer or oligomer having more than two polymerizable groups, and an initiator. The polymer precursor mixture may also comprise one or more additional iodinated monofunctional monomers, one or more additional crosslinker monomers or oligomers, and/or one or more additional monofunctional monomers. As used herein, "monofunctional" refers to a monomer containing only one polymerizable group, while "multifunctional" refers to a monomer containing more than one polymerizable group.

In an embodiment, the monofunctional iodinated monomer comprises an acrylate polymerizable group. In another embodiment, the monofunctional iodinated monomer comprises a styrene, acrylamide, or methacrylamide polymerizable group. In an embodiment, the polymerizable group is a terminal or end group.

As used herein, an iodinated monomer comprises an iodine-containing moiety. In an embodiment, the iodinated monomer comprises an iodine-containing moiety which is an iodinated aryl or heteroaryl group. In an embodiment, the iodine-containing moiety is $C_5$-$C_{30}$ aryl or $C_5$-$C_{30}$ heteroaryl having at least 1 iodine atom. In an embodiment, the iodine-containing moiety is $C_5$-$C_{30}$ aryl or $C_5$-$C_{30}$ heteroaryl having at least 2 iodine atoms. In an embodiment, the iodine-containing moiety is $C_5$-$C_{30}$ aryl or $C_5$-$C_{30}$ heteroaryl having at least 3 iodine atoms. In an embodiment, the iodine-containing moiety is $C_6$ aryl with iodine atoms attached directly to the ring, with the number of iodine atoms being from 3 to 5. The description herein can be used for embodiments using Br or Bi as radiopaque moieties.

In the description immediately below, the variables are used in the context of the immediate structures shown, as will be apparent to one of ordinary skill in the art.

In an embodiment, the repeating unit derived from the first radiopaque monomer has the general formula:

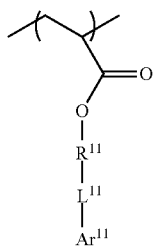

(Formula 15)

wherein $R^{11}$ is independently a substituted or unsubstituted $C_2$-$C_{36}$ alkylene group; $C_3$-$C_{36}$ cycloalkylene group; $C_2$-$C_{36}$ alkenylene group; $C_3$-$C_{36}$ cycloalkenylene group; $C_2$-$C_{36}$ alkynylene group; $C_5$-$C_{36}$ arylene group; or $C_5$-$C_{36}$ heteroarylene group;

each $L^{11}$ is independently a single bond; —(CH$_2$)$_q$—; —(HCCH)$_q$—; —O—; —S—; —SO—; —SO$_2$—; —SO$_3$—; —OSO$_2$—; —NR$^{12}$—; —CO—; —COO—; —OCO—; —OCOO—; —CONR$^{13}$—; —NR$^{14}$CO—; —OCONR$^{15}$—, —NR$^{16}$COO—, or —NR$^{17}$CONR$^{18}$—;

each $Ar^{11}$ is independently an iodine-, bromine or bismuth-containing $C_5$-$C_{36}$ aryl group containing one or more rings, or an iodine-, bromine or bismuth-containing $C_5$-$C_{36}$ heteroaryl group containing one or more rings;

each of $R^{12}$-$R^{18}$ is independently hydrogen or a $C_1$-$C_{10}$ alkyl group; each q is independently an integer selected from the range of 1 to 10. In an embodiment, $R^{11}$ is substituted or unsubstituted $C_2$-$C_{36}$ alkylene, $C_3$-$C_{36}$ cycloalkylene, $C_2$-$C_{36}$ alkenylene, $C_3$-$C_{36}$ cycloalkenylene, $C_2$-$C_{36}$ alkynylene, $C_5$-$C_{36}$ arylene, or $C_5$-$C_{36}$ heteroarylene; $L^{11}$ is a single bond, —(OH$_2$)$_n$—, —(HCCH)$_n$—, —O—, —S—, —SO—, —SO$_2$—, —SO$_3$—, —OSO$_2$—, —NR$^2$—, —CO—, —COO—, —OCO—, —OCOO—, —CONR$^3$—, —NR$^4$CO—, —OCONR$^5$—, —NR$^6$COO—, or —NR$^7$CONR$^8$—; $Ar^{11}$ is an iodinated $C_5$-$C_{36}$ aryl or $C_5$-$C_{36}$ heteroaryl; and each of $R^{12}$-$R^{18}$ is independently hydrogen or $C_1$-$C_{10}$ alkyl; n is an integer selected from the range of 1 to 10. In an embodiment, $L^{11}$ is ester or amide. In an embodiment, the first repeating unit is derived from an iodinated monofunctional monomer comprising iodinated $C_5$-$C_{36}$ aryl or $C_5$-$C_{36}$ heteroaryl.

In an embodiment, a second repeating unit in the polymer is derived from a crosslinking reagent comprising a non-iodinated multifunctional crosslinker monomer or oligomer. In another embodiment, the repeating unit derived from the crosslinker monomer has the general average formula 16-A below:

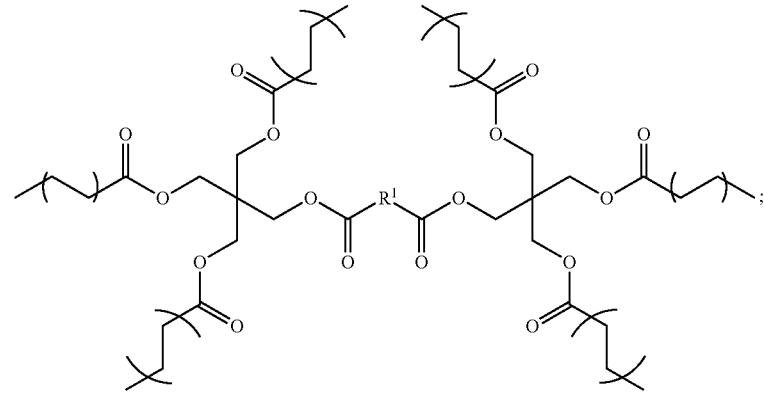

(Formula 16-A)

wherein $R^1$ is as defined for Formula 2.

In another embodiment, the repeating unit derived from the crosslinker has the average general formula (Formula 16-B), wherein $R^1$ is as defined for Formula 2. $R^7$ in Formula 6-A is substituted or unsubstituted $C_2$-$C_{36}$ alkylene, $C_3$-$C_{36}$ cycloalkylene, $C_2$-$C_{36}$ alkenylene, $C_3$-$C_{36}$ cycloalkenylene, $C_2$-$C_{36}$ alkynylene, $C_5$-$C_{36}$ arylene, $C_5$-$C_{36}$ heteroarylene, an oligomeric polyether, (Formula 3) an oligomeric polycarbonate (Formula 4), or an oligomeric polyurethane (Formula 5), wherein $R^3$ in Formula 3 is $C_4$-$C_{20}$ alkylene and n1 is an integer from 1 to 50 or wherein $R^a$ in Formula 4 is $C_3$-$C_{20}$ alkylene and n2 is an integer from 1 to 50 or wherein where $R^5$ in Formula 5 is aliphatic group, substituted or unsubstituted $C_2$-$C_{36}$ alkylene, $C_3$-$C_{36}$ cycloalkylene, $C_2$-$C_{36}$ alkenylene, $C_3$-$C_{36}$ cycloalkenylene, $C_2$-$C_{36}$ alkynylene, $C_5$-$C_{36}$ arylene, $C_5$-$C_{36}$ heteroarylene, aromatic group, polyalkyl siloxane group, polyether group, polyester group, polycarbonate group or a combination of linear or branched aliphatic groups and aromatic groups and n3 is an integer from 1 to 50.

Formula 16-B

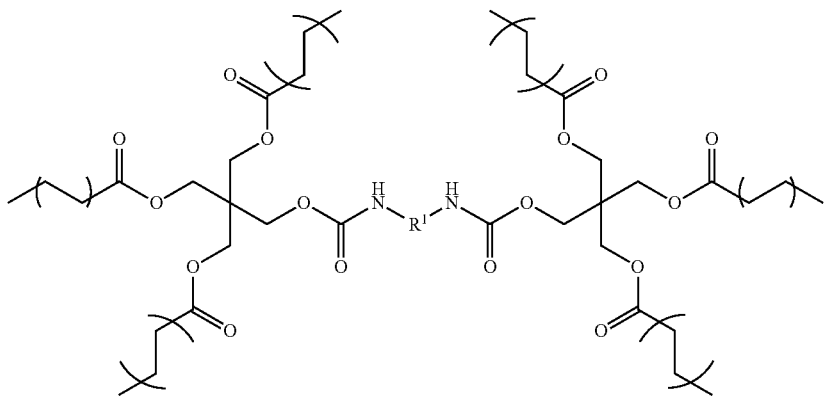

In another embodiment, the repeating unit derived from the crosslinker monomer has the general formula (Formula 16-C), wherein the pentaerythritol moieties are attached by ester linkages to a central trimesic (with 1,3,5-substitution pattern; 1,2,4-substitution is also available commercially) acid moiety that is an aromatic group and the resultant crosslinker average structure is nonafunctional (having nine functional groups).

Formula 16-C

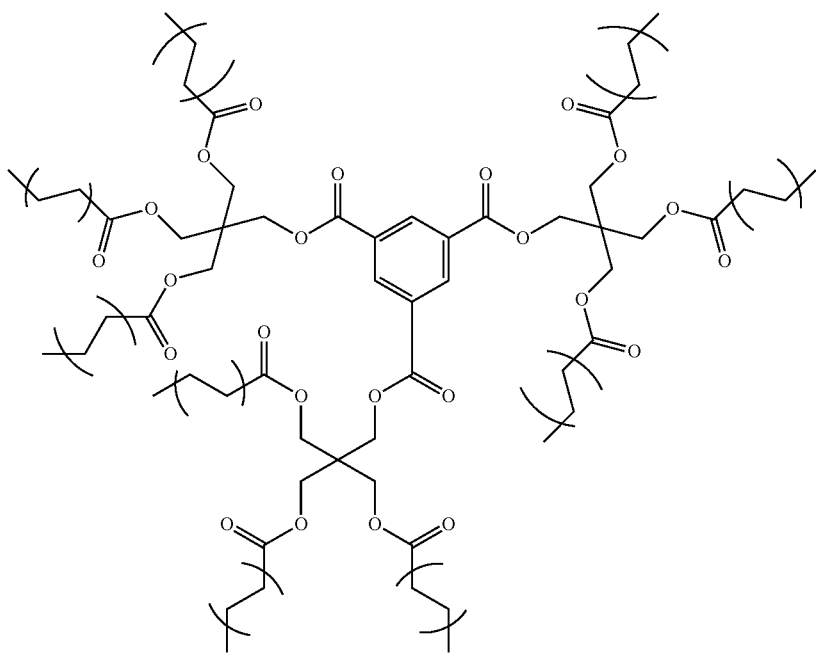

In another embodiment, the repeating unit derived from the crosslinker monomer has the general formula shown in Formula 16-D, in which a central toluene-2,4,6-triisocyanate core reacted with pentaerythritol triacrylate produces an averaged structure that is a nonafunctional crosslinker with urethane linkages to the aromatic core moiety:

Formula 16-D

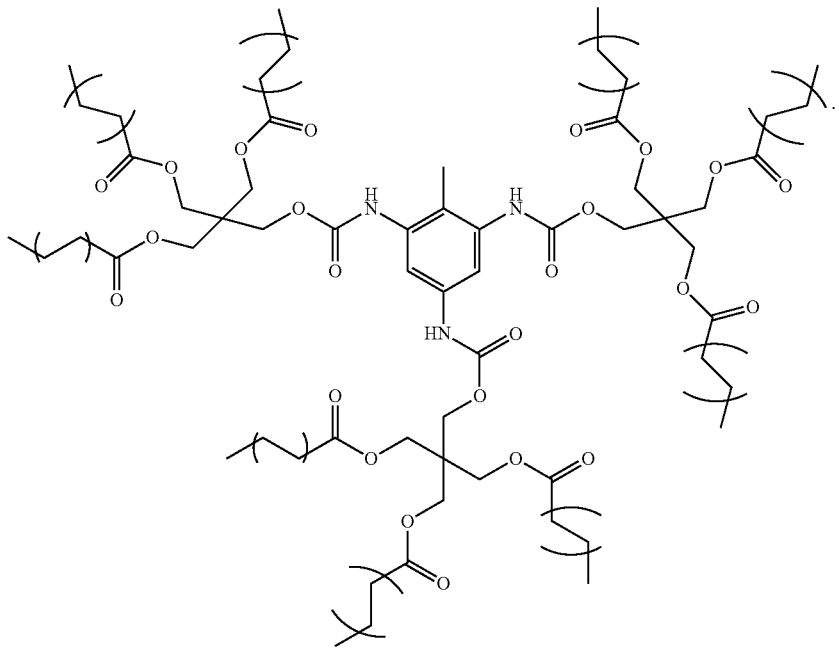

In another embodiment, the repeating unit derived from the crosslinker monomer has the general average trifunctional formula (Formula 16-E), Formula 16-E

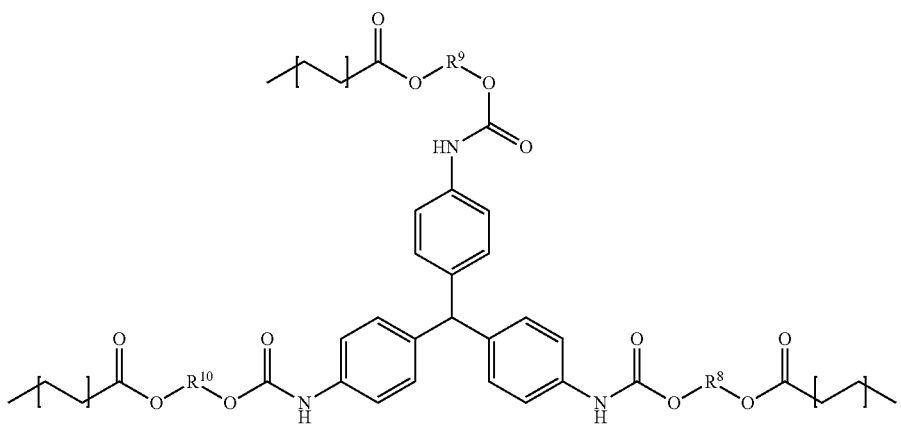

in which $R^8$, $R^9$ and $R^{10}$ are as defined for formula 2-F. As appreciated by those skilled in the art, $R^8$, $R^9$ and $R^{10}$ in Formula 16-E can be, in whole or part, substituted for the multi-functional pentaerythritol moiety seen in Formulas 16-A, 16-B, 16-C and 16-D to generate a penta-acrylate to nona-acrylate crosslinker, and the 1,1,1-tris-(4-isocyanatophenyl)-methane core of the Formula 16-E crosslinker can be substituted for the toluene 2,3,5-triisocyanate core of the Formula 16-E crosslinker. The structure shown in Formula 16-E can be optimized by adjusting the carbon number of $R^8$, $R^9$ and $R^{10}$ using the same chemistry approach used to generate the different $R^1$ segment lengths for the radiopaque iodinated monomer, and in so doing provide additional distance between crosslinks to alleviate brittleness while allowing for durable, reversible H-bonding contribution of the urethane groups to total network reinforcement.

Though Formulas 16-A, 16-B, 16-C, 16-D and 16-E are all non-iodinated and comprised in part of pentaerythritol triacrylate clustered crosslinker groups, exemplify hexa- and nona-functional acrylate clustered crosslinkers with central aromatic and non-aromatic cores and are averaged structures as assembled, the description and structures are not intended to be limiting in terms of: 1) functionality, the extreme being dendrimers with an unlimited number of branches, 2) linkage type between the polymerizable groups and the center segment, or 3) random averaged structures vs. well-defined controlled structures, as is understood by those skilled in the art.

The clustered crosslinkers in 16-A, 16-B, 16-C, 16-D and 16-E, for example, provide a means of achieving higher crosslink density than a bifunctional crosslinker while the spacer segment retains a means of imparting flexibility to avoid brittleness.

In an embodiment, the non-iodinated polyfunctional crosslinker monomer has a central segment that is an oligomeric polyester, an oligomeric polycarbonate or an oligomeric polyurethane. In an embodiment, the molecular weight of the oligomer is less than 1000. In an embodiment, the molecular weight of the oligomer is greater than or equal to 100 and less than 1000. In an embodiment, the molecular weight of the oligomer is greater than or equal to 500 and less than 1000. In an embodiment, the molecular weight of the oligomer is any molecular weight that produces a composition having properties that are useful in the desired use. In an embodiment, the molecular weight of the oligomer is greater than 1000 and less than 10,000. The molecular weight of the oligomer may be greater than 1000 and less than 2500, greater than 1500 and less than 2500, or greater than 2000 and less than 2500. In an embodiment, the dispersity or polydispersity index may be from 1.0 to 10. In an embodiment, the oligomeric center segment is a poly ($C_2$-$C_{36}$ carbonate). In another embodiment, the center segment comprises a polycondensate of one or more compounds selected from the group consisting of: diacid chloride, diol, diisocyanate, and bis-chloroformate. In an embodiment, the number of atoms in the central segment may be from 10 to 100. The compounds used to form the polycondensate can be linear or branched aliphatic, cycloaliphatic, partially cycloaliphatic or partially aromatic. In an embodiment, the compounds used to form the polycondensate may be linear or branched aliphatic or cycloaliphatic.

The polymer network may also comprise repeating units derived from at least two crosslinker monomers or oligomers, both or one of which have a functionality higher than two. The two crosslinker monomers or oligomers may be any suitable structure shown or described here. The repeating units from one of the crosslinker monomers may be derived from diacrylate crosslinker monomers. In addition to Formulas 2 and 3, the repeating units for a second crosslinker monomer of a bifunctional type may be described by Formula 17-A:

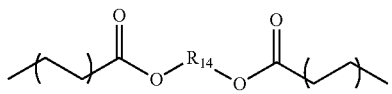

(Formula 17A)

wherein $R^{14}$ in Formula 17-A is substituted or unsubstituted $C_2$-$C_{36}$ alkylene, $C_3$-$C_{36}$ cycloalkylene, $C_2$-$C_{36}$ alkenylene, $C_3$-$C_{36}$ cycloalkenylene, $C_2$-$C_{36}$ alkynylene, $C_5$-$C_{36}$ arylene, $C_5$-$C_{36}$ heteroarylene, an oligomeric polyester, an oligomeric polycarbonate, or an oligomeric polyurethane.

The polymer network may further comprise a repeating unit derived from a monofunctional non-iodinated monomer. In an embodiment, this repeating unit may be described by Formula 5 or any suitable structure shown or described here.

In an embodiment, the cross-linked polymer network comprises a repeating unit derived from a monofunctional iodinated monomer and a repeating unit derived from a multifunctional non-iodinated crosslinker monomer or oligomer having more than two polymerizable groups. In an embodiment, the network may also comprise a repeating unit derived from a non-iodinated monofunctional co-monomer. The repeating unit derived from this co-monomer may be described by the general formula:

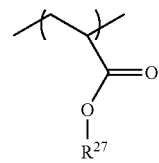

(Formula 18)

In an embodiment $R^{27}$ in Formula 18 is $C_2$ to $C_{36}$ alkyl. $R^{27}$ in Formula 18 may be branched or unbranched.

In another embodiment, the network may further comprise a repeating unit derived from an additional iodinated monomer. This repeating unit may be described by the general formula:

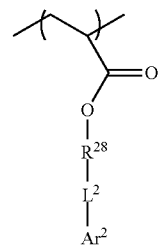

Formula 19

In an embodiment in Formula 19, $R^{28}$ is substituted or unsubstituted $C_2$-$C_{36}$ alkylene, $C_3$-$C_{36}$ cycloalkylene, $C_2$-$C_{36}$ alkenylene, $C_3$-$C_{36}$ cycloalkenylene, $C_2$-$C_{36}$ alkynylene, $C_5$-$C_{36}$ arylene, or $C_5$-$C_{36}$ heteroarylene; $L^2$ is a single bond, —$(CH_2)_n$—, —$(HCCH)_n$—, —O—, —S—, —SO—, —$SO_2$—, —$SO_3$—, —$OSO_2$—, —$NR^2$—, —CO—, —COO—, —OCO—, —OCOO—, —$CONR^3$—, —$NR^4CO$—, —$OCONR^5$—, —$NR^6COO$—, or —$NR^7CONR^8$—;

$Ar^2$ is an iodinated $C_5$-$C_{30}$ aryl or $C_5$-$C_{30}$ heteroaryl having at least 3 iodine atoms; and each of $R^2$-$R^8$ is independently hydrogen or $C_1$-$C_{10}$ alkyl;

n is an integer selected from the range of 1 to 10 and $R^{28}$ is other than $R^{11}$.

In embodiments, there is more than one crosslinker included in a composition. Examples of additional crosslinker monomers that can be included to any useful amount in the composition include: polycarbonate diacrylate, C10 diacrylate, and multiple others as described in WO 2012/019145, for example, along with the clustered crosslinkers described herein. In an embodiment, there is more than one crosslinker as described herein used in a composition.

In another aspect, the invention also provides methods for making radiopaque polymers comprising a crosslinked network. In an embodiment, the method comprises the steps of forming a polymer precursor mixture comprising one or more first monomers described herein, one or more crosslinker monomers or oligomers described herein, a free radical initiator; and polymerizing the polymer precursor mixture.

In a specific embodiment, the method comprises the steps of:
a) forming a polymer precursor mixture comprising
i) a first monomer having the general structure

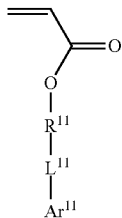

Formula 1

$R^{11}$ is independently a substituted or unsubstituted $C_2$-$C_{36}$ alkylene group; $C_3$-$C_{36}$ cycloalkylene group; $C_2$-$C_{36}$ alkenylene group; $C_3$-$C_{36}$ cycloalkenylene group; $C_2$-$C_{36}$ alkynylene group; $C_5$-$C_{36}$ arylene group; or $C_5$-$C_{36}$ heteroarylene group;

each $L^{11}$ is independently a single bond; —(CH$_2$)$_q$—; —(HCCH)$_q$—; —O—; —S—; —SO—; —SO$_2$—; —SO$_3$—; —OSO$_2$—; —NR$^{12}$—; —CO—; —COO—; —OCO—; —OCOO—; —CONR$^{13}$—; —NR$^{14}$CO—; —OCONR$^{15}$—, —NR$^{16}$COO—, or —NR$^{17}$CONR$^{18}$—;

each $Ar^{11}$ is independently an iodine-, bromine or bismuth-containing $C_5$-$C_{36}$ aryl group containing one or more rings, or an iodine-, bromine or bismuth-containing $C_5$-$C_{36}$ heteroaryl group containing one or more rings;

each of $R^{12}$-$R^{18}$ is independently hydrogen or a $C_1$-$C_{10}$ alkyl group;

each q is independently an integer selected from the range of 1 to 10;

a second monomer having the general average structure

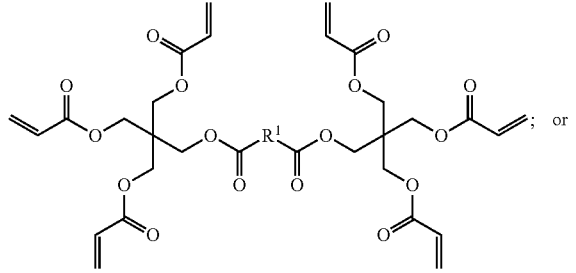

Formula 6-A

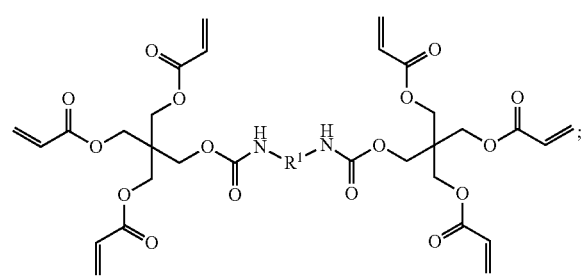

Formula 6-B wherein $R^1$ is substituted or unsubstituted $C_2$-$C_{36}$ alkylene, $C_3$-$C_{36}$ cycloalkylene, $C_2$-$C_{36}$ alkenylene, $C_3$-$C_{36}$ cycloalkenylene, $C_2$-$C_{36}$ alkynylene, $C_5$-$C_{36}$ arylene, $C_5$-$C_{36}$ heteroarylene, an oligomeric polyester, an oligomeric polycarbonate, an oligomeric polyurethane;

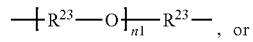

Formula 3

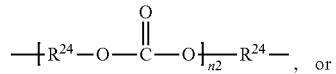

Formula 4-

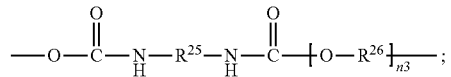

Formula 5

Wherein $R^{23}$ is as defined for Formula 3 above, $R^{24}$ is as defined for Formula 4 above and $R^{25}$ and $R^{26}$ are as defined for Formula 5 above and
ii) a free radical initiator; and
b) polymerizing the polymer precursor mixture.

In an embodiment, a first monomer is an iodinated monomer having one of the structures shown below:

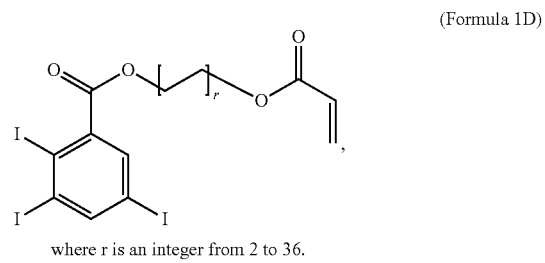

(Formula 1D)

where r is an integer from 2 to 36.

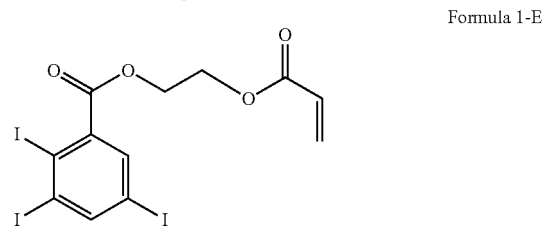 [SMILES: C=CC(=O)OCCOC(=O)c1cc(I)cc(I)c1I]

Formula 1-E

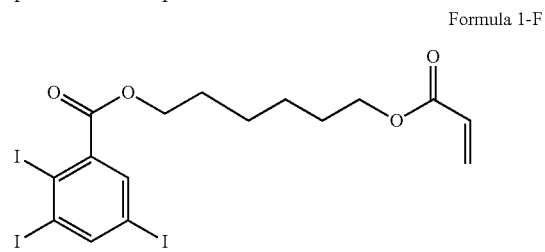

Formula 1-F

The crosslinker monomer or oligomer, in combination with the other monomers in the mixture, allows formation of a crosslinked network. The structure and amount of crosslinker(s) in the polymer precursor mixture may be selected to provide a sufficiently high crosslink density to achieve the desired modulus in the composition. In different embodiments, the molecular weight of the crosslinker is in the range from 100 to 1000, 200 to 2000 or 200-5000, or any other useful molecular weight range. Blends of crosslinkers can allow shorter and longer crosslinkers to be used together.

In an embodiment, the multifunctional crosslinker monomer or oligomer comprises a plurality of acrylate polymerizable groups. In another embodiment, the multifunctional iodinated monomer comprises a plurality of styrene, acrylamide, or methacrylamide polymerizable groups.

In an embodiment, the crosslinker monomer or oligomer may be classified as "hydrophobic". In an embodiment, a hydrophobic monomer or oligomer may be defined as being insoluble in water. In an embodiment, the crosslinker monomer or oligomer is less soluble in water than a poly(ethylene glycol) di(meth)acrylate of comparable molecular weight.

An optional monofunctional non-iodinated co-monomer can be used to adjust the properties of the polymer. For example, the co-monomer can be used to modify the glass transition temperature (Tg) of the polymer. As another example, the co-monomer can be selected to assist in system compatibilization.

In an embodiment, the co-monomer is a vinyl monomer. A wide range of commercially-available vinyl monomers can be utilized, including but not limited to butyl acrylate, which imparts a Tg value near −40° C. Such a low glass transition temperature can help to offset the typically higher Tg contribution of radiopaque monomer and crosslinkers having relatively low molecular weight values. The amenability of a wide cross section of vinyl monomers to polymerization or copolymerization by a free radical mechanism facilitates access to useful structure-property modifications.

In an embodiment, the monofunctional co-monomer comprises an acrylate polymerizable group. In another embodiment, the monofunctional co-monomer comprises a styrene, acrylamide, or methacrylamide polymerizable group. In an embodiment, the polymerizable group is an end group. Though styrene monomers typically do not polymerize as aggressively and to as high a conversion as acrylates, in copolymerization reactions with acrylates styrene monomers propagate more readily and can be used to good advantage where required. In different embodiments, the amount of comonomer may be at least 50 wt %. In different embodiments, the amount of comonomer may be from 50-90 wt %, 50-80 wt %, 60-80 wt %, 60-90 wt %, 2.5-90 wt %, 5-50 wt %, 5-25 wt %, 25-50 wt %, 50-80 wt %, 10-50 wt %, 20-50 wt %, 50-99 wt %, 90-near 100 wt %, or 50-70 wt %, or any other range producing a functional end-product. In different embodiments, the amount of comonomer may be from 2.5-90 wt %, 5-80 wt %, 10-80 wt %, 20-90 wt %, 2.5-10 wt %, 5-50 wt %, 5-25 wt %, 25-50 wt %, 50-80 wt %, 10-50 wt %, 20-50 wt %, or 10-70 wt %, or any other range producing a functional end-product. In an embodiment, the comonomer is not present.

In an embodiment, the number of repeating units in any repeating unit described or shown herein is not specifically limited, but is rather any number that is functionally feasible, that is, can be synthesized and has the desired use in the desired compositions, compounds, methods and devices. As a non-limiting example, the number of repeating units in the first repeating is between 1 and 10,000 in an embodiment. As a non-limiting example, the number of repeating units in the second repeating is between 5 and 10,000 in an embodiment.

In an aspect, more than one monomer or oligomer is used to form repeating units characterized as first repeating unit, second repeating unit, etc. I In an embodiment of this aspect, the weight percentage of the first repeating unit is from 1-100 wt %, the weight percentage of the second repeating unit is from 5 to 90 wt % and the weight percentage of the third repeating unit is from 0 to 75 wt %. In an embodiment of this aspect, the weight percentage of the first repeating unit is from 20-90 wt %, the weight percentage of the second repeating unit is from 5 to 75 wt % and the weight percentage of the third repeating unit is from 5 to 75 wt %. In an embodiment of this aspect, the weight percentage of the first repeating unit is from 50-85 wt %, the weight percentage of the second repeating unit is from 10 to 55 wt % and the weight percentage of the third repeating unit is from 0 to 55 wt %. In an embodiment of this aspect, the weight percentage of the first repeating unit is from 30-75 wt %, the weight percentage of the second repeating unit is from 10 to 50 wt % and the weight percentage of the third repeating unit is from 10 to 50 wt %. In an embodiment of this aspect, the amount of the second repeating unit is between 65 and 85 wt %. As is recognized, any permutation of the components described that produces a functional final product can be used, even if not specifically described herein. In an embodiment of this aspect, the weight percentage of the first repeating unit is from 10-50 wt %, the weight percentage of the second repeating unit is from 65 to 85 wt %. In an embodiment of this aspect, the weight percentage of the first repeating unit is from 10-90 wt %, the weight percentage of the second repeating unit is from 90 to 10 wt %. It is understood that all lower, intermediate and higher values and ranges are included to the same extent as if they were included separately.

In an embodiment, the amount of the first repeating unit is at least 50% of the total weight of the composition. In an embodiment, the amount of the first repeating unit is at most 50% of the total weight of the composition. In an embodiment, the amount of the first repeating unit is from 15-70 wt % of the total weight of the composition. In an embodiment, the amount of the first repeating unit is from 5-90 wt % of the total weight of the composition. In an embodiment, the amount of the first repeating unit is from 40-70 wt % of the total weight of the composition. In an embodiment, the amount of the second repeating unit is below 80 wt % of the total weight of the composition. In an embodiment, the amount of the second repeating unit is at most 50 wt % of the total weight of the composition. In an embodiment, the amount of the second repeating unit is at least 50 wt % of the total weight of the composition. In an embodiment, the amount of the second repeating unit is at most 40 wt % of the total weight of the composition. In an embodiment, the amount of the first repeating unit is from 40 wt %-70 wt % of the network, the amount of the second repeating unit is from 10 wt %-60 wt % of the network, and the amount of the third repeating unit is from 20 wt %-50 wt % of the network, with the total amounts of the first, second and third repeating units being 100 wt %. Any permutation of the components described where the total amounts of the second and third repeating units is 100 wt % can be used and is intended to be described to the same extent as if specifically described.

In an embodiment, provided is a method for making a polymer composition comprising a crosslinked network, the method comprising the steps of: a) forming a polymer precursor mixture comprising a first monomer as described herein, a crosslinker monomer or oligomer as described herein, and a free radical initiator; and b) polymerizing the polymer precursor mixture. In an embodiment, the polymer precursor mixture is substantially homogeneous.

In an embodiment, the amount of the radiopaque monomer in the monomer mixture is at least 5-10 wt %. In an embodiment, the amount of the radiopaque monomer in the polymer precursor mixture is at least 20 wt %. In an embodiment, the amount of the radiopaque monomer in the polymer precursor mixture is at least 25 wt %. In an embodiment, the amount of the radiopaque monomer in the polymer precursor mixture is at least 30 wt %. In an embodiment, the amount of the radiopaque monomer in the polymer precursor mixture is at least 50 wt % and can even reach 100%. In an embodiment, the amount of the crosslinker in the polymer precursor mixture is less than or equal to 80 wt %. In an embodiment, the amount of the crosslinker in the polymer precursor r mixture is less than or equal to 90 wt %. In an embodiment, the amount of the crosslinker in the polymer precursor mixture is less than or equal to 75 wt %. In another embodiment, the polymer precursor mixture comprises 40%-70 wt % of radiopaque monomer(s), 10-40 wt % crosslinker, and 20-50 wt % added co-monomer with the total amount including photoinitiator or other free radical initiator being 100 wt %. In an embodiment, the amount of initiator is less than 1 wt %. In an embodiment, the polymer precursor mixture comprises at least 60 wt % radiopaque monomer(s), and less than or equal to 40 wt % crosslinker (s). In an embodiment, the polymer precursor mixture comprises at least 50 wt % radiopaque monomer(s), and less 50 wt % crosslinker(s). As will be understood, any permutation of the components that produces a functional compound or composition can be used.

A wide range of free radical initiating systems may be used for polymerization. In different embodiments, the initiator may be a photoinitiator, a thermal initiator or a redox (reduction oxidation) initiator. Photoinitiating systems are particularly useful, provided that a photoinitiator is chosen that does not require wavelengths of light that are absorbed excessively by the base monomer ingredients of the formulation. Irgacure 819 (Ciba (BASF), Bis(2,4,6-trimethylbenzoyl)-phenylphosphineoxide) is one example of a photoinitiator that has been found to be particularly useful for the curing system.

Photopolymerization occurs when monomer solution is exposed to light of sufficient power and of a wavelength capable of initiating polymerization. The wavelengths and power of light useful to initiate polymerization depends on the initiator used. Light used in the invention includes any wavelength and power capable of initiating polymerization. Preferred wavelengths of light include ultraviolet. In different embodiments, the light source primarily provides light having a wavelength from 200 to 500 nm or from 200 to 400 nm. In an embodiment, 1-100 mW/cm$^2$ of 200-500 nm light is applied for a time from 10 sec to 60 mins. Any suitable source may be used, including laser sources. The source may be filtered to the desired wavelength band. The source may be broadband or narrowband, or a combination. The light source may provide continuous or pulsed light during the process.

Thermal initiating systems, with low-temperature or high-temperature initiators, common examples being benzoyl peroxide and azobisisobutyronitrile (AIBN), are also useful in situations where a particularly large or irregularly-shaped object that is difficult to illuminate uniformly is to be prepared. Also of use in the latter scenario are free radical initiating systems that produce free radicals by any type of redox reaction, such as the Fenton system involving ferrous salts with tert-butyl hydroperoxide, or other metal-organic, organic such as triethylamine+hydroperoxides, or photo-organic redox systems, an example of the latter being the Eosin-Y+triethanolamine visible light initiating system.

A number of pseudo-living free radical polymerization systems, some of which are capable of producing polymers with narrower molecular weight distributions than conventional free radical polymerizations, are also described in the art and can be amenable to production of crosslinker segments for SMPs or for SMP curing. For example, styrene monomers that polymerize to low conversion in a conventional system may be driven to high conversion in a pseudo-living system. These pseudo-living systems typically involve variable combinations of reversible chain propagation-termination and/or chain transfer steps. "Living" free radical polymerizations known to the art include, but are not limited to, NMP, RAFT, and ATRP.

Additionally; any other type of non-conventional free radical polymerization process, whether pseudo-living or not, that produces free radicals capable of initiating polymerization of the radiopaque and non-radiopaque monomers and crosslinkers comprising the SMPs of this invention, fall within the scope of potential initiating-polymerization methods. These and other free radical initiating systems are conceivable and known to those skilled in the art.

In embodiments, examples of the useful initiating systems include anionic, cationic, free radical polymerizations that are non-living, pseudo-living or living as well as Ziegler-Natta and olefin metathesis. The use of these systems is known in the art. In an embodiment, these systems are useful if a prepolymerized segment is at least difunctional and has hydroxyl or other groups known in the art which can be used to attach polymerizable groups, including acrylate groups in an embodiment.

In an embodiment, some or all of the components of the polymer precursor mixture are combined at a temperature greater than ambient temperature. In different embodiments, the initiator may be added at the same time as the monomer components or added just prior to or at the time of molding. In another embodiment where a thermal initiator is used, the polymer precursor mixture ingredients may be divided into two parts; wherein the high storage temperature ingredients are in Part A, and the lower storage temperature ingredients are in Part B. The thermal initiator may be added to the lower storage temperature ingredients in Part B at a storage temperature that is below the initiator's polymerization temperature. In an embodiment, forming the polymer precursor mixture (or a portion of the polymer precursor mixture) at greater than ambient temperature can assist in maintaining solubility of the polymer precursor mixture components, thereby enabling formation of a homogenous mixture.

In an embodiment, the polymer precursor mixture is held at a temperature greater than ambient temperature during free radical polymerization. In an embodiment, the polymer precursor mixture is held a temperature between 65° C. and 150° C. or from 65° C. and 100° C. during the polymerization step. In an embodiment, a pre-cure step is performed in a vacuum environment. In separate embodiments, the curing step is performed using free radical, anionic, cationic, Diels-alder, thiol-ene, polycondensation, or other mechanisms known in the art. During molding, pressure may be applied during polymerization to ensure mold filling.

In an embodiment, an additional curing or heat treatment step is employed after the polymerization step (e.g. after photopolymerization). In an embodiment, the cured parts are removed from the mold and then undergo additional curing operations through exposure to elevated temperatures. In an embodiment, the curing temperature is from 50° C. and 150° C. and the curing time from 5 seconds to 60 minutes during this additional step.

In different embodiments, the amount of functional group conversion is at least 30%, 40%, 50%, 60%, 70%, 80% or 90% or higher. In an embodiment, the amount of extractables is less than or equal to 1% or less than or equal to 0.5%. In an embodiment, the amount of extractables is less than or equal to 5%. In an embodiment, the amount of extractables is less than or equal to 3%. In an embodiment, the amount of extractables is less than or equal to 2%. In an embodiment, the amount of extractables is determined by isopropanol extraction.

As used herein, a crystalline material displays long range order. The crystallinity of polymers is characterized by their degree of crystallinity, or weight or volume fraction of crystalline material in the sample ranging from zero for a completely non-crystalline polymer to one for a theoretical completely crystalline polymer.

If a polymer is semicrystalline, shape change can be hindered and slowed, and performance of devices incorporating the polymer can become clinically unacceptable. In an embodiment, the polymer compositions of the invention are considered substantially amorphous. As used herein, substantially amorphous is defined as the absence of crystalline features as detected by differential scanning calorimetry (DSC), or by inconsistency and lack of reproducibility in mechanical tensile test results, e.g. stress-strain curve at a fixed temperature. In an embodiment, lack of reproducibility may be indicated by reproducibility of less than 95% at 95% confidence interval. A substantially amorphous polymer may incorporate relatively small amounts of crystallinity. As is typical of amorphous polymers, the substantially amorphous polymer compositions of the invention show a transition from a glassy state to a rubbery state over a glass transition temperature range. Crystallinity can be reduced or eliminated by reducing the concentration of specific monomers that enhance this condition, and/or by introducing dissimilar structures to ensure that the polymer's molecular structure doesn't align during polymerization to result in crystallinity.

In an embodiment, the monomers and oligomers (including crosslinker monomers or oligomers) used to form the radiopaque polymer are selected to assure compatibility (e.g. homogeneity after polymerization). In an embodiment, the radiopaque polymer is sufficiently homogenous in terms of solid-phase compatibility of the polymerized units and in the sufficiently random incorporation of units throughout polymerization to obtain the desired performance characteristics. Phase incompatibility can lead to voids in the SMP morphology. Voids in the SMP matrix compromise mechanical performance and can lead to uptake of water and other fluids that displace the generated void volume, even when the incompatible phases are hydrophobic or even "water-repellant." Excessively non-random incorporation of comonomers, especially diacrylate or other polyacrylate crosslinkers, as polymerization proceeds from low conversion to high conversion can lead to a non-uniform crosslink density, with regions of higher (brittle) and lower (rubbery) crosslink density.

In an embodiment, the radiopaque polymer is homogenous enough that repeatable results (95% reproducible data at 95% confidence interval) can be obtained in a simple ultimate tensile test at a fixed temperature. In an embodiment, homogeneity of the polymer may be improved by selection of the components of the monomer solution to reduce phase separation in the liquid or solid state. In addition, the monomer components and polymerization technique may be selected to facilitate random incorporation of monomer and crosslinker groups by free radical polymerization during the cure. In an embodiment, the same type of polymerizable groups is present in each of the monomers. For example, for monomers and ologimers (and crosslinker monomers) having acrylate polymerizable groups and aliphatic hydrocarbon linkers, the inductive effect exerted upon the acrylate group by the typically aliphatic linker attachments is expected to be similar.

In many applications, biodurability can be defined as durability for the period of time necessary to assure that the body has overcome the need of the device's function, e.g. a fallopian tube occlusion device that relies upon scar tissue formation to close the lumen no longer needs the device to generate scar tissue once the lumen is fully closed. If that period of time is 90 days, for example, then the biodurable life of the device can be this value plus a suitable safety factor used in the design. Biodurability then is the ability of the device, and its material, to withstand the environmental challenges at its location of placement in the body, e.g. if in the bloodstream, it must withstand a bloody environment. In an embodiment, the radiopaque polymer is not biodegradable within the desired lifetime of the medical device. In another embodiment, the radiopaque polymer is not biodegradable within three years. In an embodiment, the non-biodegradable polymer does not include aromatic groups other than those present in naturally occurring amino acid. In an embodiment, the non-biodegradable polymer does not contain esters that are readily hydrolyzed at physiological pH and temperature.

For almost all locations within the body, one of the several primary mechanisms of degradation can be caused by absorption of water or moisture. Whether the environment contains interstitial fluids, blood, saliva, urine, bile, intracranial fluid, etc., these environments are aqueous based. If the device or its material absorbs water, the material properties and device dimensions can change due to swelling, or the device function can be affected, such as the autogenesis of an errant electrical path, or the material properties can degrade causing the device to weaken or break apart. Therefore a primary consideration for biodurability of an implanted device is the device and all of its material's ability to not absorb water.

In an embodiment, water uptake, or water absorption, can change the device's characteristics or detrimentally affect the device's performance over its intended life. In an embodiment, medical devices fabricated from the polymers of the invention will exhibit minimal water uptake. The water uptake can be measured over a test period equivalent to the lifetime or the device or can be measured over a shorter screening period. In an embodiment, the extent of water uptake is <1% by weight over 24 hours. For devices which exhibit water uptake of greater than 1% by weight over 24 hours, typically continuous exposure results in material changes such as brittleness and eventual mechanical failure in standard testing.

The minimal level of iodine concentration needed to achieve sufficient radiopacity to provide clinically acceptable imaging may be determined empirically. In an embodiment, evaluation of identically sized devices formulated from polymers using different weight percentages of iodinated monomer can be compared under simulated clinical use conditions. Using physicians' subjective review and correlating their opinion with the results from an image analysis program, Image J, to quantify signal levels, clinically imaging quality is correlated with iodine concentration. The result is a determination of the minimum iodine concentration to assure acceptable image quality. In an embodiment, the minimum iodine concentration value was established at 511 mg/cm$^3$. In an embodiment, the minimum iodine concentration value is above 200 mg/cm$^3$. In an embodiment, the iodine concentration value is between 50 and 600 mg/cm$^3$. As is recognized in the art, the radiopaque atom incorporation range for suitable visualization is dependent on the configuration of the device. In an embodiment, the first repeating unit contains the radiopaque atom(s) and is present in an amount of above 15 wt % of the network. In an embodiment, the first repeating unit contains the radiopaque atom(s) and is present in an amount of above 20 wt % of the network. In an embodiment, the first repeating unit contains the radiopaque atom(s) and is present in an amount of above 30 wt % of the network. In an embodiment, any incorporation of radiopaque moieties that produces a functional product can be used. As described elsewhere, the radiopaque atom(s) can include atoms other than iodine, including bromine or bismuth.

In another embodiment, the signal obtained from a radiopaque polymer device may be compared with that of a platinum device of similar dimensions. In an embodiment where signal level is obtained by X-ray under a 6 inch water phantom, the signal from the radiopaque polymer device may be 70%-90% or 80%-90% of that of the platinum device.

Any polymer that can recover an original shape from a temporary shape by application of a stimulus such as temperature is considered a SMP. The original shape is set by processing and the temporary shape is set by thermo-mechanical deformation. A SMP has the ability to recover large deformation upon heating. Shape memory functionality can be utilized to develop medical devices that can be introduced into the body in a less invasive form, wherein the pre-deployed, or temporary, shape is intentionally smaller, or thinner, resulting in a lower profile and a smaller opening (smaller catheter or incision) to introduce the device into the patient than would otherwise be required without the shape change functionality. Then, when stimulated by temperature, typically body temperature but can also be greater than body temperature, the device undergoes shape recovery to return to its permanent, larger form.

A polymer is a SMP if the original shape of the polymer is recovered by heating it above a shape recovery temperature, or deformation temperature ($T_d$), even if the original molded shape of the polymer is destroyed mechanically at a lower temperature than $T_d$, or if the memorized shape is recoverable by application of another stimulus. Any polymer that can recover an original shape from a temporary shape by application of a stimulus such as temperature may be considered a SMP.

From a biomedical device perspective, there are characteristics that are considered favorable in device design. They are quantified in terms of stimuli (such as temperature) driven response, well-defined response temperature, modulus, and elongation. In an embodiment, the thermomechanical properties of the shape memory polymer used to form the device are optimized for one or more of the following: Rubbery modulus (Erub), Glass transition temperature (Tg), and Speed of recovery (S).

The preferred ranges of rubbery modulus can be different for different applications. The range of moduli of biological tissue can vary from 20 GPa (bone) to 1 kPa (eye) In an embodiment, the rubbery modulus is between 0.1 MPa and 15 MPa at 37° C. In an embodiment, the rubbery modulus is between 0.1 MPa and 50 MPa for the flexible state and between 0.1 to 500 MPa for the rigid state at 37° C. Any rubbery modulus value that produces a functional product can be used. By polymer formulation adjustments, the SMP's modulus, e.g. stiffness, can be established as very soft, on the order of 0.1 MPa. In one embodiment, for use as a device such as an embolic coil, this soft material enhances compaction of the coil pack, shortening the resulting pack for easier placement and ultimately increasing the speed of occlusion. Through other formulations, a higher value can be achieved for the SMP's modulus, such as 15 MPa, to enhance stiffness. In another embodiment, stiffer SMPs can be used to form a tube stent wherein localized stiffness is used to generate outward radial force against a vessel wall when deployed which is required for retention.

In an embodiment, the polymers are selected based on the desired glass transition temperature(s) (if at least one segment is amorphous) taking into consideration the environment of use. In one method, the polymer transition temperature is tailored to allow recovery at the body temperature, $T_r \sim T_g \sim 37°$ C. (A. Lendlein and R. Langer, "Biodegradable, elastic shape-memory polymers for potential biomedical applications." Science, vol. 296, pp. 1673-1676, 2002). The distinct advantage of this approach is the utilization of the body's thermal energy to naturally activate the material. The disadvantage of this approach, for some applications, is that the mechanical properties (e.g., stiffness) of the material are strongly dependent on $T_g$, and can be difficult to alter in the device design process. In particular, it would be difficult to design an extremely stiff device when the polymer $T_g$ is close to the body temperature due to the compliant nature of the polymer. Another possible disadvantage is that the required storage temperature, $T_s$, of a shape memory polymer with $T_g \sim 37°$ C. will typically be below room temperature requiring "cold" storage prior to deployment. In different embodiments, the glass transition temperature of the SMP of the present invention as determined from the peak of tan δ is 75° C., 50° C., 45° C. or any useful temperature. In general, as low a glass transition temperature is best, as understood in the art with the desired applications. In different embodiments, the glass transition temperature may be below body temperature (e.g. 25-35° C.), near body temperature (32-42° C.) or above body temperature (40-50° C.). Any Tg value that produces a functional product can be used.

The storage modulus of at least partially non-crystalline polymers decreases in the glass transition region. DMA results highlight the changes that occur as the material is heated from its storage temperature ($T_s$)) to its response temperature ($T_r$) and above. Methods are known in the art to determine relevant values to describe SMPs including thermal mechanical analysis (TMA) and differential scanning calorimetry (DSC); TMA and DSC are heating rate dependent. Such methods are described for example in WO 2012/019145, hereby incorporated by reference.

Typically, for each medical device application that incorporates shape recovery, the clinician is anticipating relatively rapid and repeatable shape recovery. In an embodiment, the shape memory polymer devices of the invention produce shape recovery that is fast enough to be detected, completes in a reasonable (intraoperative) time, and repeatable from one device to another. In an embodiment, the shape recovery time can be measured in use or from a screening procedure. The shape recovery time can be measured either from release to 100% recovery or from release to a predetermined amount of recovery.

The rate of shape change correlates with the rate of storage modulus change on the DMA curve between the operating temperature and $T_r$. For SMPs, rate of shape change can be primarily affected by the temperature difference between $T_o$, the operating temperature (external heating or body core temperature if self actuated), and the polymer's $T_g$ (derived from the formulation). $T_o$ is typically set above $T_r$. Typically, a larger difference between these temperatures will produce a faster rate of change up to an inherent rate limit, or asymptote of the change rate, of the material and device. This limit can be identified by monitoring shape change response time at different temperatures and plotting this relationship. Typically, the amount of response time decreases until it reaches an asymptote. The corresponding $T_o$ reflects the lowest, optimum temperature for the fastest rate of shape change for that material. Increasing the temperature above this point does not induce further reductions in the shape change recover time, e.g. does not further increase the rate of shape change. In an embodiment this inherent limit, or asymptote begins when $T_o$ is set at the temperature at which the Tan Delta curve is about 60% of its maximum value. In an embodiment, the polymer's maximum rate of shape change occurs at an environmental operating temperature (To) that is coincident with the temperature above Tg at which the material's Tan Delta value is equal to 60% of its peak value. The device may be designed so that this optimum temperature is at a useful operating temperature for the device (e.g. at body temperature or another preselected temperature).

In an embodiment, the device is operated at a temperature which is the lowest temperature at which no further increase in shape change rate is seen. In another embodiment, the device is operated at a temperature which is within +/−5° C. of this optimum temperature.

In different embodiments, the recovery ratio of the SMPs employed in the biomedical devices of the invention is greater than 75%, 80%, 90%, 95%, from 80-100%, from 90-100%, or from 95-100%. In various embodiments, the maximum achievable strain is of the radiopaque SMP from 10% to 800%, from 10% to 200%, from 10% to 500%, from 10% to 100%, from 20% to 800%, from 20% to 500%, from 20% to 800%. as measured at a temperature above the glass transition temperature. In different embodiments, the maximum achievable strain or strain to failure of the radiopaque SMP is at least 30% at least 40%, at least 50%, at least 60%, or at least 70%, from 40% to 100%, from 40% to 60%, from 50% to 100%, from 60% to 100% as measured below the glass transition temperature. In different embodiments, the maximum achievable strain or strain to failure of the SMP is at least 30% at least 40%, at least 50%, at least 60%, or at least 70%, from 40% to 100%, from 40% to 60%, from 50% to 100%, from 60% to 100% as measured at ambient temperature (20-25° C.).

In general, the ability of the device (whether technically shape memory or not) to change conformation or configuration (e.g. to expand) is made possible by manufacturing a device having a first conformation or configuration (initial configuration) and, thereafter configuring the device into a second conformation or configuration (temporary or storage configuration), wherein this configuration is at least partially reversible upon the occurrence of a triggering event. After the triggering event, the device assumes a third configuration. In an embodiment, the third configuration (deployed configuration) is substantially similar to the first configuration. However, for an implanted medical device, the device may be constrained from assuming its initial shape (first configuration). In an embodiment, the device is capable of self-expansion to the desired dimensions under physiological conditions.

The invention can provide a variety of radiopaque polymer devices for medical applications, these devices incorporating the polymer compositions of the invention. In different embodiments, these devices can be for purposes of an indwelling, permanent implant to provide the function of: opening, or maintaining an open anatomical lumen; closing an anatomical lumen, either partially as a valve, or complete lumen occlusion for any physiological fluid or gas flow or for a applied therapeutic fluid or gas flow; support of an anatomical structure to assist in therapeutic restoration of an organ, vascular, digestive, excrement, or airway function; support of an anatomical structure to assist in therapeutic restoration of an orthopaedic, maxillofacial, spinal, joint or other skeletal or function; to support hemostasis by covering an area inside the body after tissue dissection or resection, a patch, such as for hemostasis of the liver, or other organ, In other embodiments, these devices can be used for purposes of a diagnostic or therapeutic instrument or device to provide the function of: a catheter for the purposes of accessing an anatomical location; delivering another device and/or therapeutic agent; or controlling the access or delivery of another device and/or therapeutic agent; a temporarily indwelling device to provide a limited time therapeutic benefit, such as a vena cava filter that is placed in a vessel, left indwelling for a period of time, for example to capture blood clots, and subsequently removed when the therapeutic period is completed.

In one embodiment for neurovascular cases, wherein intracranial aneurysms are repaired, current state of care may use very fine metal (platinum) based embolic coils delivered into the aneurysm sack to fill this space and effect an isolation of the weakened vessel wall from the parent vessel thereby reducing the risk of rupture and stroke. However, because of the metal nature of these devices, two deficiencies typically occur: 1. Approximately 25% of these patients must return for retreatment as the aneurysm continues to grow, and 2. To diagnose the need for retreatment, many of these patients must have an invasive angiogram (contrast injection) of the aneurysm area under fluoroscopy to be able to visualize the condition given that the metal coil materials are not compatible with MRI or CT Scan imaging modalities. A non-metallic, radiopaque SMP embolic device for aneurysm repair does not suffer this limitation in imaging capability.

Although the description herein contains many specificities, these should not be construed as limiting the scope of the invention but as merely providing illustrations of some of the presently preferred embodiments of the invention. For example, thus the scope of the invention should be determined by the appended claims and their equivalents, rather than by the examples given. If any variable is not defined, the variable takes any definition that will allow the group or moiety to be synthesized and function in the desired way, as determined by one of ordinary skill in the art by the context and other information provided herein.

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

All patents and publications mentioned in the specification are indicative of the levels of skill of those skilled in the art to which the invention pertains. References cited herein are incorporated by reference herein in their entirety to indicate the state of the art, in some cases as of their filing date, and it is intended that this information can be employed herein, if needed, to exclude (for example, to disclaim) specific embodiments that are in the prior art. For example, when a compound is claimed, it should be understood that compounds known in the prior art, including certain compounds disclosed in the references disclosed herein (particularly in referenced patent documents), are not intended to be included in the claim.

When a compound or composition is claimed, it should be understood that compounds or compositions known in the art including the compounds or compositions disclosed in the references disclosed herein are not intended to be included. When a Markush group or other grouping is used herein, all individual members of the group and all combinations and subcombinations possible of the group are intended to be individually included in the disclosure.

In the moieties and groups described herein, it is understood that the valence form of the group that is required to fulfill its purpose in the description or structure is included, even if not specifically listed. For example, a group that is technically a "closed shell" group as listed or described can be used as a substituent in a structure, as used herein. For every closed shell moiety or group, it is understood that a group corresponding to a non-closed structural moiety is included, for use in a structure or formula disclosed herein.

Every formulation or combination of components described or exemplified can be used to practice the invention, unless otherwise stated. Specific names of compounds are intended to be exemplary, as it is known that one of ordinary skill in the art can name the same compounds differently. When a compound is described herein such that a particular isomer or enantiomer of the compound is not specified, for example, in a formula or in a chemical name, that description is intended to include each isomers and enantiomer of the compound described individual or in any combination. One of ordinary skill in the art will appreciate that methods, device elements, starting materials, and synthetic methods, and other than those specifically exemplified can be employed in the practice of the invention without resort to undue experimentation. All art-known functional equivalents, of any such methods, device elements, starting materials, and synthetic methods are intended to be included in this invention. Whenever a range is given in the specification, for example, a temperature range, a time range, a composition range or a mechanical property range, all intermediate ranges and subranges, as well as all individual values included in the ranges given are intended to be included in the disclosure.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. Any recitation herein of the term "comprising", particularly in a description of components of a composition or in a description of elements of a device, is understood to encompass those compositions and methods consisting essentially of and consisting of the recited components or elements. The invention illustratively described herein suitably may be practiced in the absence of any element or elements, limitation or limitations which is not specifically disclosed herein.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In general the terms and phrases used herein have their art-recognized meaning, which can be found by reference to standard texts, journal references and contexts known to those skilled in the art. The preceding definitions are provided to clarify their specific use in the context of the invention.

The invention may be further understood by the following non-limiting examples.

EXAMPLES

Example 1. Polymer Formation

Methods for making polymer compositions are known in the art, including as described in WO2012/019145, incorporated by reference.

Example 2. Formation of Clustered Crosslinkers

Shown below is an exemplary synthesis of a clustered pentaerythritol triacrylate (Sartomer SR444, Sartomer USA) with spacer:

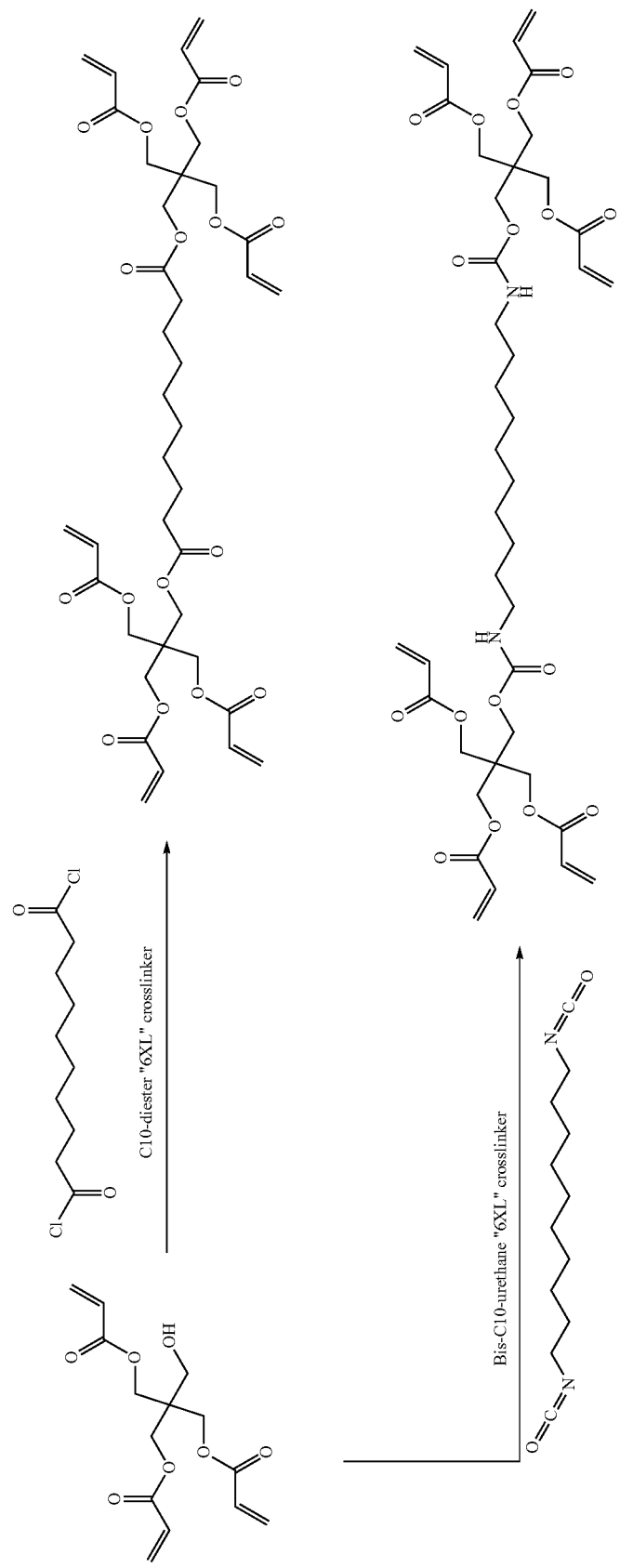

FIG. 1 shows Dynamic Mechanical Analysis (DMA) properties of a material comprised of 67% of the iodinated monomer represented by Formula 1 in which $R^{11}$ is an ethyl ($C_2$) spacer group, $L^{11}$ is an ester connecting group, and $Ar^{11}$ is a 2,3,5-triiodobenzoate group, and 33% of the clustered C-10 diester-based crosslinker described in this example. This material has a broad Tg transition centered at 77° C. and a rubbery modulus at 107° C. of 63.5 MPa. The DMA results shown in FIG. 1 reveal the desirability of reducing the Tg contribution of the iodinated monomer in order to compensate for the higher crosslink density resulting in the apparent high Tg contribution of the clustered crosslinker.

Figure 2:
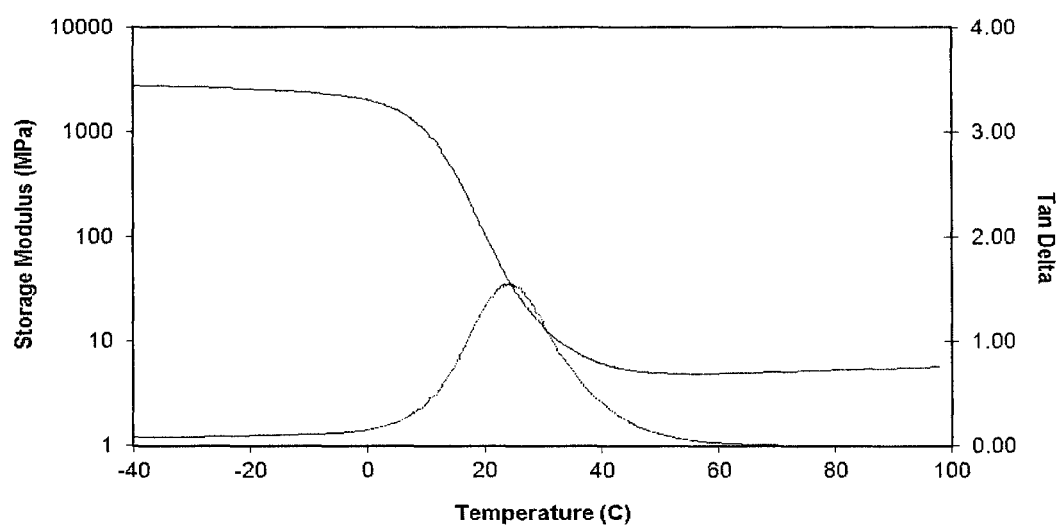
FIG. 2 shows DMA properties of the material comprised of 70% of the iodinated monomer represented by Formula 1 in which $R^{11}$ is a hexyl ($C_6$) spacer group, $L^{11}$ is an ester connecting group, and $Ar^{11}$ is a 2,3,5-triiodobenzoate group, 15% n-butyl acrylate comonomer, 12% poly(hexamethylene carbonate) diacrylate Mn 610, and 3% of the clustered crosslinker described in Example 2.

FIG. 2 shows DMA properties of the material comprised of 70% of the iodinated monomer represented by Formula 1 in which $R^{11}$ is a hexyl (C6) spacer group, $L^{11}$ is an ester connecting group, and $Ar^{11}$ is a 2,3,5-triiodobenzoate group, 15% n-butyl acrylate comonomer, 12% poly(hexamethylene carbonate) diacrylate Mn 610, and 3% of the C-10 diester-based clustered crosslinker described in this example. This material had a narrower Tg transition centered at 24° C. and a rubbery modulus at 54° C. of 5 MPa.

Figure 3:
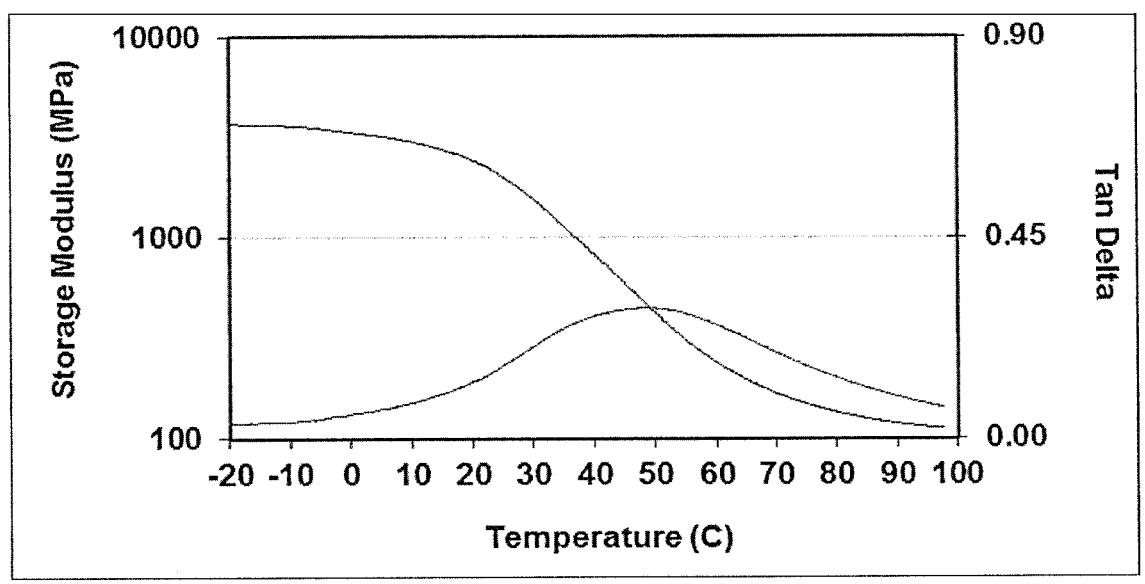
FIG. 3 shows DMA properties of the material comprised of 60% of the iodinated monomer represented by Formula 1 in which $R^{11}$ is a hexyl (C6) spacer group, $L^{11}$ is an ester connecting group, and $Ar^{11}$ is a 2,3,5-triiodobenzoate group, 20% poly(hexamethylene carbonate) diacrylate (Mn 610), and 20% of the clustered crosslinker described in Example 2.

FIG. 3 shows DMA properties of the material comprised of 60% of the iodinated monomer represented by Formula 1 in which $R^{11}$ is a hexyl (C6) spacer group, $L^{11}$ is an ester connecting group, and $Ar^{11}$ is a 2,3,5-triiodobenzoate group, 20% poly(hexamethylene carbonate) diacrylate (Mn 610), and 20% of the clustered C-10 diester-based crosslinker described in this example. This material had a broader Tg transition centered at 49° C. and a rubbery modulus at 109° C. of 110 MPa. These compositions are intended to be illustrative rather than limiting.

Example 3. Formation of Iodinated Monomers with Spacers

The synthesis of structures such as the first monomer having different chain length between the polymerizable group and iodinated ring can be performed as described herein and known in the art. As a specific example, the structure

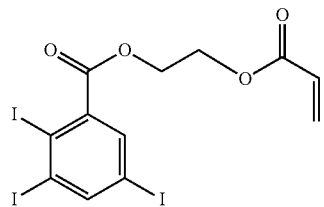

Formula 1-F can be synthesized by the following exemplary procedure.

Set-up a 500 mL multi-neck flask in a water bath with mechanical agitator, thermocouple, nitrogen purge, and condenser vented to the basic solution scrubber. Charge 70 g 2,3,5-triiodobenzoic acid (TIBA) to the flask. Then charge 30 g thionyl chloride and Charge 300 g dichloromethane to the flask. Heat the pot to reflux at 40° C. with vigorous mixing. Hold for 20 hours at temperature. There should be very little solids remaining if TIBA is converted. Distill away most of the dichloromethane at atmospheric pressure, then add 100 g toluene to the flask and vacuum to distill away the remaining thionyl chloride, allowing flask temperature to reach 55-60° C. When no longer condensing thionyl chloride, add 100 g toluene and pull a maximum vacuum of 25 in. Hg. Stop distilling when the head temperature is above 45° C. for at least 30 minutes. Charge 58 g toluene, 21 g pyridine, and 32.5 g 2-hydroxyethyl acrylate (2-HEA) to a 1 L addition funnel. Switch to air sparge and heat flask to 30° C. Begin the addition of the 2-HEA solution. The addition should take about 45 minutes and the flask temperature should be kept below 50° C. After the addition, increase the flask temperature to 45-50° C. and maintain for 1 hour. Cool the flask to room temperature and decant the product solution. Filter product solution with 1 micron filter paper to clear. Wash the product consecutively, retaining the organic layer each time, with 140 g of 3.6% hydrochloric acid solution, then with 140 g of 6.6% potassium carbonate solution, then with 140 g deionized water. Filter the organic layer with 1 micron filter paper. Place the filtered organic layer back into a clean 500 mL flask and remove toluene by heating flask to maximum temperature of 60 C and pull vacuum to strip toluene. Distill toluene until it the system is 30-35% solids. Cool the flask to room temperature. Weigh the solution. Heat the solution to about 50° C. so that it is completely dissolved. Slowly add hexane to precipitate the product. The amount of hexane should total 1.5 times the product solution weight. Chill the solution to about 5° C.

The structure below can be made by the following exemplary synthetic method:

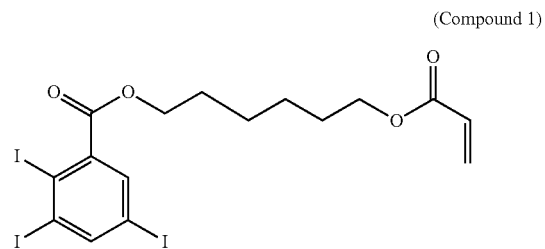 [SMILES: C=CC(=O)OCCCCCCOC(=O)c1cc(I)cc(I)c1I]

(Compound 1)

A solution of 6-bromohexanol (15 g) in anhydrous THF (85 mL) was stirred under nitrogen in a methanol/ice bath. Triethylamine (12 mL) was added slowly and the solution became cloudy. Acryloyl chloride (7.1 mL) in anhydrous THF (35 mL) was then added dropwise. The milky suspension was then warmed slowly to room temperature and stirred for 30 minutes, whereupon the reaction was judged complete by TLC ($KMnO_4$ stain). A small aliquot was removed and after small workup was analyzed by NMR to confirm completion. The reaction mixture was then diluted with methyl tert-butyl ether (MTBE) and water and the mixture partitioned. The MTBE layer was then washed successively with water three times and then with brine, and then dried with anhydrous magnesium sulfate filtered, and evaporated to afford 11.6 g of pure product. Product identity was confirmed by $^1$H-NMR and $^{13}$C-NMR. Purity was >95% by NMR. A flask containing compound 1 (11.6 g), 2,3,5-triiodobenzoic acid (TIBA; 35 g), potassium carbonate (13.5 g), and anhydrous DMF (250 mL) was heated to 85° C. under nitrogen for 90 minutes. The reaction was judged complete by TLC ($KMnO_4$ stain). The reaction mixture was cooled to room temperature and then in an ice bath for 15 minutes. To the cooled flask was added water (500 mL) and the product was extracted into MTBE (2×500 mL). The combined MTBE extracts were washed successively with water (4×500 mL) and brine (500 mL) and then dried with anhydrous magnesium sulfate, filtered, and evaporated to afford an oil which solidified upon standing. Yield: 24.2 g (73%). The product was judged >97% pure by $^1$H NMR. Product identity was confirmed by $^1$H-NMR and $^{13}$C-NMR.

Example 4. Synthesis of C8-TIA

A multi-neck flask was flushed with nitrogen and charged with 8-bromo-1-octanol (30 g) as a liquid via pipet. THF (180 mL) was added to the flask via syringe and the mixture was stirred with a magnetic stir bar. The flask was cooled in an ice/methanol bath. Triethylamine (21 mL) was added via syringe and the mixture turned cloudy. Acryloyl chloride (12.3 mL) was dissolved in THF (30 mL) and added slowly to the mixture via an addition funnel. The reaction mixture turned into a milky white suspension. After the addition was complete, the cold bath was removed and the mixture was allowed to warm to RT and stirred for 1 hour. The mixture was diluted with methyl tert-butyl ether (MTBE) and washed with water three times. The organic layer was dried over MgSO$_4$, filtered, and concentrated in vacuo to a neat liquid. The material was dried briefly under high vacuum to give 8-bromooctyl-acrylate (20.7 g, 55% yield) as a lightly colored liquid. The product was charged as a liquid via pipet into a multi-neck flask that had been flushed with nitrogen. DMF (400 mL) was poured into the flask and the mixture was stirred with a magnetic stir bar. 2,3,5-Triiodobenzoic acid (55.1 g) was added as a solid and the mixture turned darker in color. Potassium carbonate (21.8 g) was added as a solid and the reaction mixture was heated with a heating mantle to 85° C. for 2.5 hours. A small aliquot was worked up and analyzed by NMR to determine that the reaction was complete. The reaction was cooled to ambient temperature and diluted with water. The mixture was extracted with MTBE four times until TLC confirmed that almost no product remained in the aqueous layer. The combined organics were washed with water three times followed by a brine wash. The layer was dried with anhydrous MgSO$_4$, filtered, and concentrated to an oil. The oil was allowed to sit (in darkness) overnight during which time some of it precipitated into a white solid. A mixture of 10% ethyl acetate in heptane was added to dissolve the oil and triturate the solid. The solid was isolated in a Buchner funnel and dried under high vacuum to give about 8 grams of product. The filtrate was concentrated and re-dissolved in hot pentane with a minimal amount of MTBE added to get the material to dissolve. The mixture was allowed to cool slowly to ambient temperature and then the flask was placed in a freezer for 1 hour. A white solid precipitated during this time. The cold suspension was briefly sonicated to precipitate more material. The solid was collected on a Buchner funnel, rinsed with a small amount of pentane, and dried under high vacuum to give ~12.5 grams of product that was checked by NMR. The filtrate was concentrated to give about 20 grams of product as an oil. The material was dissolved in DCM and adsorbed onto silica gel. The material was purified via silica gel vacuum chromatography using 0% to 5% to 10% ethyl acetate in heptane as eluent. The fractions containing the product spot were isolated and concentrated in vacuo to give an oil. The oil was dissolved in hot pentane with a minimal amount of MTBE to dissolve the material. The flask was allowed to slowly cool to RT and then stored in a freezer overnight. More solid had precipitated during this time. The solid was collected on a Buchner funnel, rinsed with a minimal amount of pentane, and dried under high vacuum to give ~14 g of product that was checked by NMR. All of the batches were combined to give ~35 g (~66% yield) of 2,3,5-Triiodobenzoic acid-8-acryloyloxy-octyl ester as a white solid. The product was characterized by $^1$H NMR, $^{13}$C NMR, LC-MS, and melting point analysis.

Example 5. Synthesis of 6XLE Crosslinker

Charge pentaerythritol triacrylate (19.97 g) to a pressure-equalizing addition funnel fitted with a Drie-Rite drying tube and add anhydrous pyridine (3.0 mL), then dissolve both to 100 mL in the funnel with anhydrous dichloromethane. In a 1000 mL 3-neck round-bottom flask, dissolve sebacoyl chloride (3.99 g) to 500 mL with anhydrous dichloromethane. While stirring the sebacoyl chloride solution, add the pentaerythritol triacrylate-pyridine solution at an average rate of 2.5 mL/min, keeping the exotherm below 26° C. At the end of the addition, reflux the system for 2 hours, then extract sequentially with 175 mL quantities of 0.5N HCl, 0.5 M Na$_2$CO$_3$ and distilled water. Dry the organic phase with 10 g anhydrous magnesium sulfate and filter through fluted filter paper into 1000 mL round-bottom flask. Remove excess dichloromethane on rotary evaporator; transfer solution into 50 mL round-bottom flask and finish solvent removal on rotary evaporator. Add a magnetic stir bar to the 50 mL round-bottom flask and sparge with nitrogen for 3 hours while stirring the viscous solution magnetically. Add acetone (3.0 mL), distilled water (1.0 mL) and pyridine (3.0 mL) to the 50 mL flask and stir at 50° C. for 1 hour. Extract solution sequentially with 175 mL quantities of 0.5N HCl, 0.5 M Na$_2$CO$_3$ and distilled water. Dry the organic phase with 10 g anhydrous magnesium sulfate and filter through fluted filter paper into 1000 mL round-bottom flask. Remove excess dichloromethane on rotary evaporator; transfer solution into 50 mL round-bottom flask and finish solvent removal on rotary evaporator. Add a magnetic stir bar to the 50 mL round-bottom flask and sparge with nitrogen for 3 hours while stirring the viscous solution magnetically. Remove stir bar from flask; yield 16.7 g (73%).

Example 6. Synthesis of PC-2110H

Charge to a 1000 mL 3-neck flask fitted with a Drie-Rite drying tube 50 g poly(hexamethylene carbonate) diol (MW 2,000), 250 mL anhydrous dichloromethane, and 8.3 mL triethylamine. Stir with a magnetic stir bar until homogeneous. Add 4.5 mL acryloyl chloride in two portions of 2.0 mL and 2.5 mL, keeping exotherm below 34° C. Reflux system in flask for 2 hours, then extract with 175 mL quantities of 0.1N HCl, 0.1M Na$_2$CO$_3$ and saturated NaCl in distilled water. Dry the organic phase with 10 g anhydrous magnesium sulfate and filter through fluted filter paper into 1000 mL round-bottom flask. Remove excess dichloromethane on rotary evaporator; transfer solution into 250 mL round-bottom flask and finish solvent removal on rotary evaporator. Add a magnetic stir bar to the 250 mL round-bottom flask and sparge with nitrogen for 3 hours while stirring the solution magnetically with the flask immersed in a 60° C. water bath to prevent the crosslinker from solidifying. Yield: 46 g.

Example 7. SMP with 6XLE and PC-2110H Crosslinker

Figure 4:
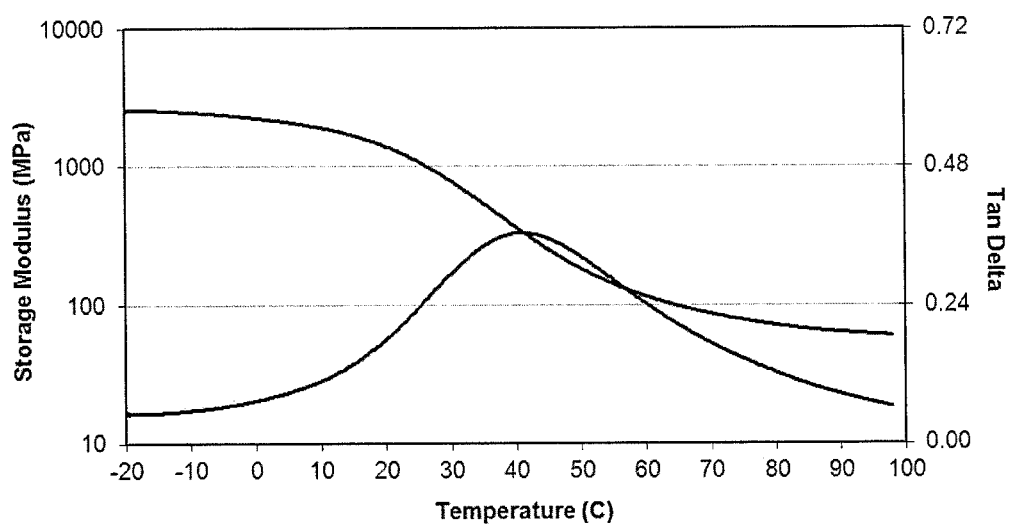
FIG. 4 shows DMA properties for a material formed by polymerizing an iodinated monomer represented by Formula 1 in which $R^{11}$ is a hexyl (C6) spacer group, $L^{11}$ is an ester connecting group, and $Ar^{11}$ is a 2,3,5-triiodobenzoate group, a poly(hexamethylene carbonate) diacrylate and the clustered crosslinker described in Example 5.

A 5 mL vial was charged with C8-TIA (3.50 g), 6XLE (0.90 g) and PC-2110H (0.60 g). The vial contents were melted and mixed to form a homogeneous melt. Then Luperox P (30 µL) was added, mixed into the melt thoroughly, and the mixture was injected into a DMA specimen mold and cured at 125° C. for two hours. DMA results (FIG. 4): Tg: 41.0° C.; storage modulus at Tg: 336 MPa; rubbery modulus at 71° C.: 84 MPa.

Example 8. Synthesis of Poly(tetrahydrofuran)-diacrylate (MW 1,110; pTHF-1 K)

To a 1000 mL 3-neck flask with a Drie-Rite drying tube add 100 g poly(tetrahydrofuran) diol (MW 1,000), 400 mL anhydrous dichloromethane, and 31 mL triethylamine. Stir with a magnetic stir bar until homogeneous. Dissolve 17 mL acryloyl chloride to 100 mL with anhydrous dichloromethane in a pressure-equalizing addition funnel. Add the acryloyl chloride solution to the stirring flask contents while keeping the exotherm temperature below 30° C. Reflux system in flask for 2 hours, then extract with 250 mL quantities of 0.1N HCl, 0.1 M $Na_2CO_3$ and saturated NaCl in distilled water. Dry the organic phase with 10 g anhydrous magnesium sulfate and filter through fluted filter paper into 1000 mL round-bottom flask. Remove excess dichloromethane on rotary evaporator; transfer solution into 250 mL round-bottom flask and finish solvent removal on rotary evaporator. Add a magnetic stir bar to the 250 mL round-bottom flask and sparge with nitrogen for 3 hours while stirring the solution magnetically with the flask immersed in a 60° C. water bath to prevent the crosslinker from solidifying. Yield: 92 g.

Example 9. SMP with Sartomer CN2302, SR399 and pTHF-1 K Crosslinkers

Figure 5:
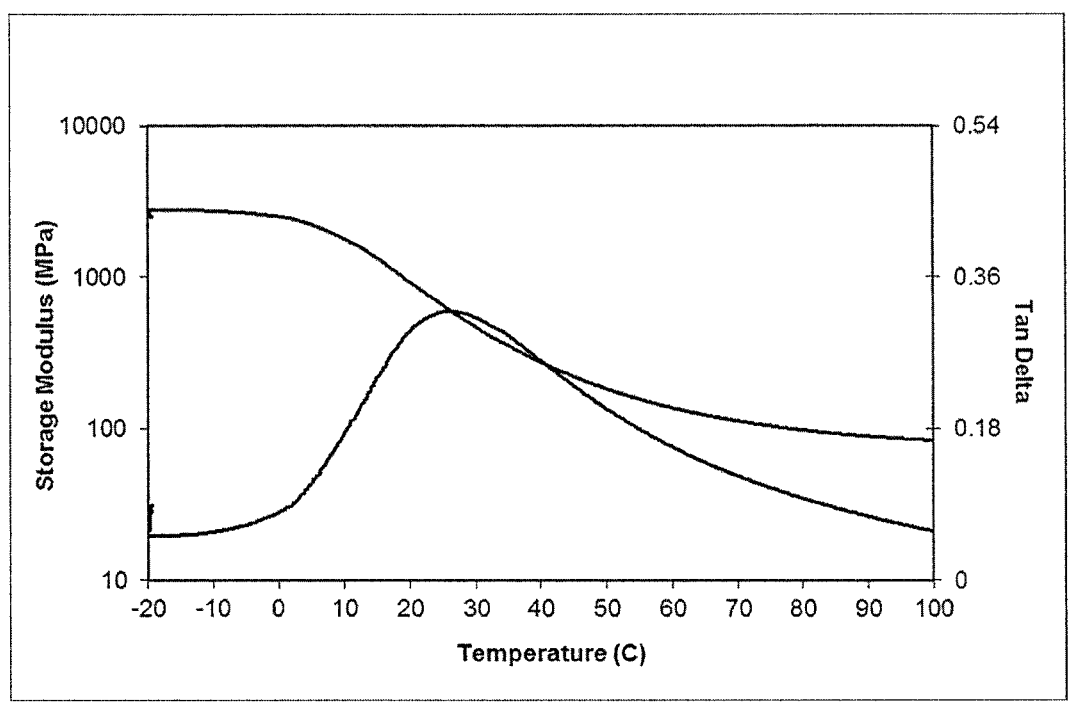
FIG. 5 shows DMA properties for a material formed by polymerizing iodinated monomers represented by Formula 1 with C11 and C12 spacer groups, a hyperbranched polyester acrylate oligomer, and dipentaerythritol pentaacrylate.

A 5 mL vial was charged with a 1:1 w:w mixture of C11-TIA and C12-TIA (4.0 g), Sartomer CN2302 (0.50 g), Sartomer SR399 (0.40 g), and pTHF-1 K (0.10 g). Sartomer CN2302 is described by the manufacturer as a hyperbranched polyester acrylate. SR 399 is described as dipentaertyritol pentaacrylate. The components were melted at 125° C. and a vacuum was applied to remove entrapped air in the system. Then Luperox P (30 µL) was added, mixed thoroughly, and the molten mixture was injected into a DMA specimen mold and cured at 125° C. for two hours. DMA results (FIG. 5): Tg: 25.8° C.; storage modulus at Tg: 617 MPa; rubbery modulus at 55.8° C.: 153 MPa.

Example 10. Synthesis of 6-Hydroxyhexyl-acrylate (HHA)

A multi-neck flask was flushed with nitrogen and charged with 6-bromo-1-octanol (26 g). The product was charged as a liquid via pipet into a multi-neck flask that had been flushed with nitrogen. DMF (400 mL) was poured into the flask and the mixture was stirred with a magnetic stir bar. 2,3,5-Triiodobenzoic acid (71.8 g) was added as a solid and the mixture turned darker in color. Potassium carbonate (19.8 g) was added as a solid and the reaction mixture was heated with a heating mantle to 85° C. for 2.5 hours. A small aliquot was worked up and analyzed by NMR to determine that the reaction was complete.

Example 11. Exemplary Radiopaque Polymer Device

Shape memory polymer devices of the invention can incorporate material formulations that utilize a suitable glass transition temperature within a range about body core temperature. To achieve different performance requirements, the polymer's $T_g$ may be intentionally suppressed below body temperature resulting in shape change occurrence immediately upon release from any physical constriction.

Non-metallic Radiopaque polymers provide a significant clinical benefit in providing good visibility of the device using common imaging techniques such as fluoroscopy, CAT-scan, and MRI. However, the material's non-metallic nature uniquely enables imaging without the typical generation of an imaging artifact, in both Cat-Scan and MRI modalities, common with metal based devices that obscures the physician's ability to view key anatomy.

In one embodiment, a radiopaque SMP with a $T_g$ of 25° C. has been utilized to accelerate the rate of shape change of an embolic coil upon expulsion from a small lumen catheter. One form of embolic devices forms a large curl of 10 mm in diameter but is constructed of an SMP wire that is only 0.032" in diameter. The wire can be formed into a pre-deployed curled shape that is straightened to allow delivery of these devices in a small diameter catheter (<5 fr). When deployed into the blood stream, these devices recovered their curl shape to effectively occlude a 9 mm vessel, with the 1 mm oversize assuring sufficient radial force from the material modulus and deflection to provide effective anchoring so that the embolic device doesn't migrate under the influence of blood flow in the vessel. A variety of coil shapes, coil diameters, curl shapes and curl diameters can leverage this capability.

Likewise, the polymer's Tg may be set above body temperature wherein an external heating device is used to provide the physician with a discretionary shape change function. In another embodiment, an SMP with a $T_g$ of 50° C. has been used to place and accurately position a tube stent within an anatomical lumen. Maintaining its low profile, predeployed temporary shape benefits the physician's ability to move and accurately locate the device prior to deployment. When held in the desired position, the device is heated to its $T_r$ by flushing with warmed saline irrigation which causes shape recovery to occur to the stent's permanent shape.

Yet, another embodiment is the use of an SMP with an elevated $T_g$ of 42° C. (just above body core temperature) that is used as a clasp for retaining a deployed device. In its permanent shape, the clasp is open, in its temporary shape, the clasp is closed. The clasp connects a device, such as a vena cava filter, the filter itself may be made from a different SMP, to a delivery guidewire that contains electrical conductors joined to a heating element adjacent to the clasp. With the SMP clasp closed in its temporary shape (below $T_g$), the device is advanced into the bloodstream. Upon reaching its desired position, the clasp is heated through an external low voltage passing down the conductors and through the heating element. Upon the temperature reaching $T_r$, the clasp opens to its recovered, permanent shape, releasing the vena cava filter.

In an embodiment, an SMP with an elevated $T_g$ of 42° C. (just above body core temperature) is used within a section of a mono-directional catheter. The catheter section is formed with a permanent curved shape to allow specific direction of the tip of the catheter. As a straight catheter is easier to manipulate into position, the temporary shape is straight but not necessarily stiff. Upon entry into the body, below $T_g$, the straight catheter is easily manipulated to a target location wherein it is warmed by an externally heated, internal delivery wire, or by warmed saline solution flushed through the catheter. Upon the material temperature reaching $T_r$, the catheter section curls, returning to its recovered, permanent shape, providing specific direction for the catheter tip during use. Meanwhile, the curvature is not so stiff as to preclude simply retrieving the catheter after use.

We claim:

1. A polymer composition comprising a crosslinked network, the network comprising
   a) a plurality of first repeating units derived from a first reagent, the first reagent comprising a monomer having the structure of Formula 1, Formula 1-A, Formula 1-B or Formula 1-C;

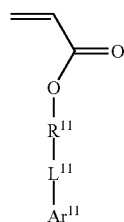

Formula 1

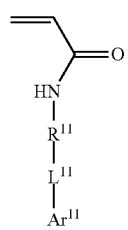

Formula 1-A

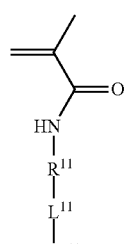

Formula 1-B

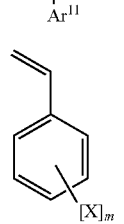

Formula 1-C wherein
X is Br or I;
m in Formula 1-C is 1-5;
each $R^{11}$ is independently a substituted or unsubstituted $C_2$-$C_{36}$ alkylene group; $C_3$-$C_{36}$ cycloalkylene group; $C_2$-$C_{36}$ alkenylene group; $C_3$-$C_{36}$ cycloalkenylene group; $C_2$-$C_{36}$ alkynylene group; $C_5$-$C_{36}$ arylene group; or $C_5$-$C_{36}$ heteroarylene group;
each $L^{11}$ is independently a single bond; —(CH$_2$)$_q$—; —(HCCH)$_q$—; —O—; —S—; —SO—; —SO$_2$—; —SO$_3$—; —OSO$_2$—; —NR$^{12}$—; —CO—; —COO—; —OCO—; —OCOO—; —CONR$^{13}$—; —NR$^{14}$CO—; —OCONR$^{15}$—, —NR$^{16}$COO—, or —NR$^{17}$CONR$^{18}$—;
each $Ar^{11}$ is independently an iodine-, bromine or bismuth-containing $C_5$-$C_{36}$ aryl group containing one or more rings, or an iodine-, bromine or bismuth-containing $C_5$-$C_{36}$ heteroaryl group containing one or more rings;

each of $R^{12}$-$R^{18}$ is independently hydrogen or a $C_1$-$C_{10}$ alkyl group;
each q is independently an integer selected from the range of 1 to 10;

b) a plurality of second repeating units derived from a second reagent, the second reagent comprising a branched monomer or oligomer comprising at least three terminal polymerizable groups but not comprising iodine, bromine or bismuth, wherein the branched monomer of the second reagent comprises a central portion $R^1$ linked to at least two end portions, $Y^1$ and $Y^2$, at least one of the end portions being branched, wherein both $Y^1$ and $Y^2$ are represented by the structure of

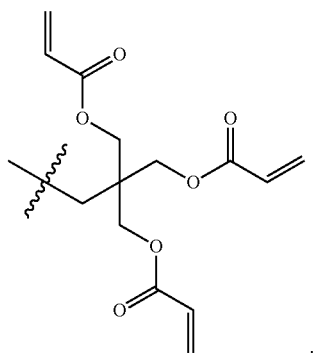

(Formula 20)

; or

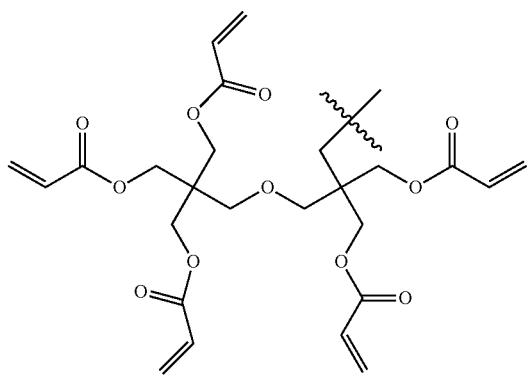

(Formula 21)

wherein
$R^1$ is $C_6$ to $C_{20}$ alkylene, and
wherein the central portion $R^1$ is linked to the end portions $Y^1$ and $Y^2$ through linker $L^1$, wherein $L^1$ is a single bond, —(CH$_2$)$_n$—, —(HCCH)$_n$—, —O—, —S—, —SO—, —SO$_2$—, —SO$_3$—, —OSO$_2$—, —NR$^3$—, —CO—, —COO—, —OCO—, —OCOO—, —CONR$^4$—, —NR$^5$CO—, —OCONR$^6$—, —NR$^7$COO—, or —NR$^8$CONR$^9$ and each of $R^3$-$R^9$ is independently hydrogen or $C_1$-$C_{10}$ alkyl; and c) a plurality of third repeating units derived from a third reagent, the third reagent comprising a monomer having at least two terminal polymerizable groups.

2. The polymer composition of claim 1, wherein the second reagent comprises a branched monomer selected from the group consisting of:

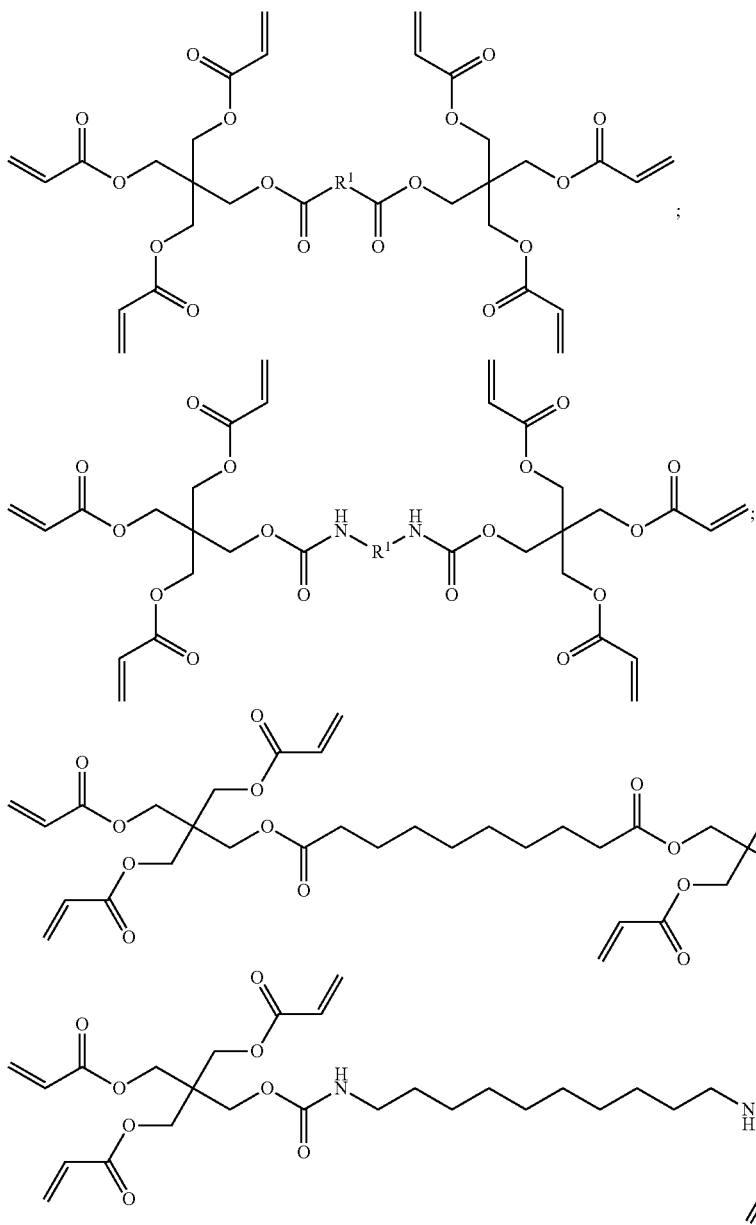

3. The polymer composition of claim 1, wherein the monomer of the first reagent has the formula

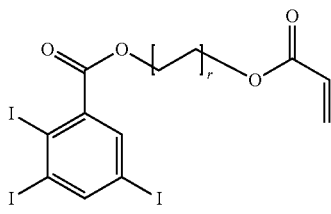

where r is an integer from 2 to 18.

4. The polymer composition of claim 3, wherein r is from 3 to 8.

5. The polymer composition of claim 1, wherein from 60 to 90 wt % of the first reagent is present in the composition.

6. The polymer composition of claim 1, wherein the third reagent comprises a monomer having the structure of Formula 14:

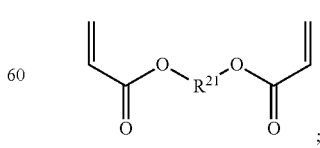

Formula 14 wherein $R^{21}$ is a substituted or unsubstituted $C_2$-$C_{36}$ alkylene group; $C_3$-$C_{36}$ cycloalkylene group; $C_2$-$C_{36}$ alkenylene group; $C_3$-$C_{36}$ cycloalkenylene group;

$C_2$-$C_{36}$ alkynylene group; $C_5$-$C_{36}$ arylene group; $C_5$-$C_{36}$ heteroarylene group; Formula 3; Formula 4 or Formula 5;

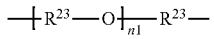

(Formula 3)

where in Formula 3, each $R^{23}$ is independently a C4-C20 alkylene group and each n1 is independently an integer from 1 to 50;

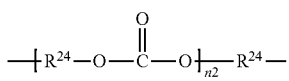

(Formula 4)

where in Formula 4, each $R^{24}$ is independently a C3-C20 alkylene group and each n2 is independently an integer from 1 to 50.

7. The polymer composition of claim 1, wherein from 60 to 90 wt % of the plurality of first repeating units are present in the crosslinked network.

8. A method of making a crosslinked polymer composition, the method comprising the steps of:

a) forming a polymer precursor mixture comprising i) a first reagent comprising a monomer having the structure of Formula 1, Formula 1-A, Formula 1-B or Formula 1-C;

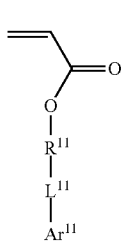

Formula 1

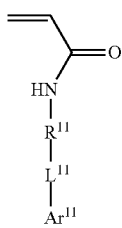

Formula 1-A

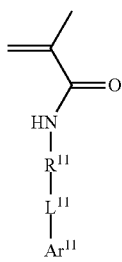

Formula 1-B

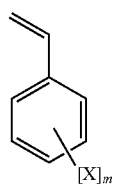

Formula 1-C wherein

X is Br or I;

m in Formula 1-C is 1-5;

each $R^{11}$ is independently a substituted or unsubstituted $C_2$-$C_{36}$ alkylene group; $C_3$-$C_{36}$ cycloalkylene group; $C_2$-$C_{36}$ alkenylene group; $C_3$-$C_{36}$ cycloalkenylene group; $C_2$-$C_{36}$ alkynylene group; $C_5$-$C_{36}$ arylene group; or $C_5$-$C_{36}$ heteroarylene group;

each $L^{11}$ is independently a single bond; —(CH$_2$)$_q$—; —(HCCH)$_q$—; —O—; —S—; —SO—; —SO$_2$—; —SO$_3$—; —OSO$_2$—; —NR$^{12}$—; —CO—; —COO—; —OCO—; —OCOO—; —CONR$^{13}$—; —NR$^{14}$CO—; —OCONR$^{15}$—, —NR$^{16}$COO—, or —NR$^{17}$CONR$^{18}$—;

each $Ar^{11}$ is independently an iodine-, bromine or bismuth-containing $C_5$-$C_{36}$ aryl group containing one or more rings, or an iodine-, bromine or bismuth-containing $C_5$-$C_{36}$ heteroaryl group containing one or more rings;

each of $R^{12}$-$R^{18}$ is independently hydrogen or a $C_1$-$C_{10}$ alkyl group;

each q is independently an integer selected from the range of 1 to 10;

ii) a second reagent comprising a branched monomer or oligomer comprising at least three terminal polymerizable groups but not comprising iodine, bromine or bismuth, wherein the branched monomer of the second reagent comprises a central portion $R^1$ linked to at least two end portions, $Y^1$ and $Y^2$, at least one of the end portions being branched, wherein both $Y^1$ and $Y^2$ are represented by the structure of

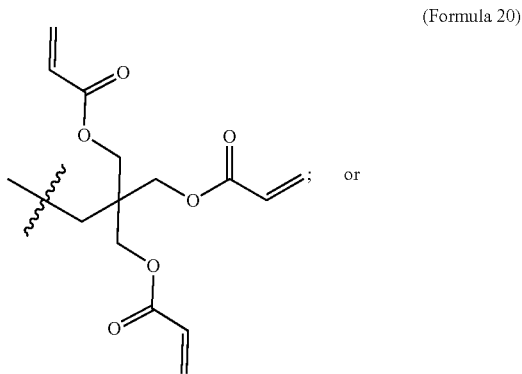

(Formula 20)

(Formula 21)

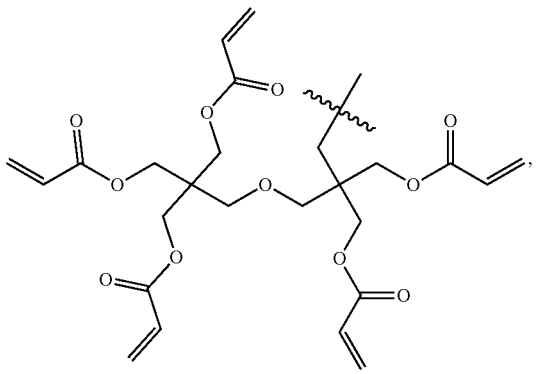

wherein
R¹ is $C_6$ to $C_{20}$ alkylene, and
wherein the central portion R¹ is linked to the end portions Y¹ and Y² through linker L¹, wherein L¹ is a single bond, —$(CH_2)_n$—, —$(HCCH)_n$—, —O—, —S—, —SO—, —$SO_2$—, —$SO_3$—, —$OSO_2$—, —NR³—, —CO—, —COO—, —OCO—, —OCOO—, —CONR⁴—, —NR⁵CO—, —OCONR⁶—, —NR⁷COO—, or —NR⁸CONR⁹ and each of R³-R⁹ is independently hydrogen or $C_1$-$C_{10}$ alkyl; and iii) a third reagent comprising a monomer having at least two terminal polymerizable groups, and b) polymerizing the polymer precursor mixture with an initiator.

9. The method of claim 8, wherein from 60 to 90 wt % of the first reagent is present in the polymer precursor mixture.

10. A radiopaque polymer device for medical applications, the device or a device feature comprising a polymer composition according to claim 1.

11. The device of claim 10 wherein the polymer exhibits a glass transition temperature (Tg) and a Tan Delta (Loss Modulus/Storage Modulus ratio) curve related to temperature; the polymer's maximum rate of shape change occurs at an environmental operating temperature (To) that is coincident with the temperature at which the material's Tan Delta value is ≤60% of its peak value, above Tg.

12. The device of claim 10 for purposes of an indwelling, permanent implant to provide the function of:
  a. opening, or maintaining an open anatomical lumen; or
  b. closing an anatomical lumen, either partially as a valve, or complete lumen occlusion for any physiological fluid or gas flow or for an applied therapeutic fluid or gas flow; or
  c. support of an anatomical structure to assist in therapeutic restoration of an organ, vascular, digestive, excrement, or airway function; or
  d. support of an anatomical structure to assist in therapeutic restoration of an orthopaedic, maxiofacial, spinal, joint or other skeletal or function; or
  e. to support hemostasis by covering an area after tissue dissection or resection, a patch.

13. The device of claim 10 for purposes of a diagnostic or therapeutic instrument or device to provide the function of:
  a. a catheter for the purposes of accessing an anatomical location; delivering another device and/or therapeutic agent; or controlling the access or delivery of another device and/or therapeutic agent; or
  b. a temporarily indwelling device to provide a limited time therapeutic benefit left indwelling for a period of time and subsequently removed when the therapeutic period is completed.

14. The polymer composition of claim 1, wherein $Ar^{11}$ is an iodine containing $C_6$ aryl with 3 to 5 iodine atoms attached directly to the aryl ring.

15. The polymer composition of claim 14 wherein $R^{11}$ is an $C_6$-$C_{36}$ alkylene group.

16. The polymer composition of claim 14, wherein $R^{11}$ is an $C_6$-$C_{24}$ alkylene group.

* * * * *